(12) United States Patent
Skidmore et al.

(10) Patent No.: US 8,443,294 B2
(45) Date of Patent: May 14, 2013

(54) VISUAL INDICATION OF ALARMS ON A VENTILATOR GRAPHICAL USER INTERFACE

(75) Inventors: John Skidmore, San Diego, CA (US);
Mark Brecht, Imperial Beach, CA (US);
Jim Fissel, Dallas, TX (US)

(73) Assignee: Covidien LP, Mansfield, MA (US)

( * ) Notice: Subject to any disclaimer, the term of this patent is extended or adjusted under 35 U.S.C. 154(b) by 144 days.

(21) Appl. No.: 12/970,696

(22) Filed: Dec. 16, 2010

(65) Prior Publication Data
US 2011/0154241 A1 Jun. 23, 2011

Related U.S. Application Data

(60) Provisional application No. 61/287,914, filed on Dec. 18, 2009.

(51) Int. Cl.
*G06F 3/048* (2006.01)
(52) U.S. Cl.
USPC ............................ 715/764; 715/771; 600/529
(58) Field of Classification Search .................. 715/771, 715/764, 808; 128/204.18, 23, 24; 600/529
See application file for complete search history.

(56) References Cited

U.S. PATENT DOCUMENTS

| | | | |
|---|---|---|---|
| 3,577,984 A | 5/1971 | Levy et al. | |
| 3,659,590 A | 5/1972 | Jones et al. | |
| 3,871,371 A | 3/1975 | Weigl | |
| 3,940,742 A | 2/1976 | Hudspeth et al. | |
| 3,961,624 A | 6/1976 | Weigl | |
| 3,961,627 A | 6/1976 | Ernst et al. | |
| 3,977,394 A | 8/1976 | Jones et al. | |
| 3,991,304 A | 11/1976 | Hillsman | |
| 3,996,928 A | 12/1976 | Marx | |
| 4,034,743 A | 7/1977 | Greenwood et al. | |
| 4,036,217 A | 7/1977 | Ito et al. | |
| 4,053,951 A | 10/1977 | Hudspeth et al. | |

(Continued)

FOREIGN PATENT DOCUMENTS

| | | |
|---|---|---|
| EP | 0414777 | 3/1991 |
| EP | 1374938 | 1/2004 |

(Continued)

OTHER PUBLICATIONS

PCT The International Search Report, Date of Mailing Apr. 7, 2011, Applicant's File Reference H-RM-01984WO, International Application No. PCT/US2010/060871, International Filing Date Dec. 16, 2010, Applicant Nellcor Puritan Bennett LLC.

(Continued)

*Primary Examiner* — Phenuel Salomon

(57) ABSTRACT

This disclosure describes systems and methods for displaying alarms to a clinician in a ventilatory system. Specifically, embodiments described herein seek to optimize the informative presentation of alarms on a ventilator interface. Embodiments of the present disclosure may provide one or more selection elements, each selection element indicating a ranked alarm event. The ranking of an alarm event may be determined by alarm level. If two alarm events are associated with the same alarm level, the ranking of the alarm events may be determined by parameter priority. Alarm event ranking is communicated by display in a hierarchical structure. When an alarm event ranking changes, the alarm event may shift up or down the hierarchical structure, depending on whether the ranking increased or decreased.

17 Claims, 6 Drawing Sheets

U.S. PATENT DOCUMENTS

| | | |
|---|---|---|
| 4,090,513 A | 5/1978 | Togawa |
| 4,112,931 A | 9/1978 | Burns |
| 4,187,842 A | 2/1980 | Schreiber |
| 4,215,409 A | 7/1980 | Strowe |
| 4,241,739 A | 12/1980 | Elson |
| 4,258,718 A | 3/1981 | Goldman |
| 4,296,756 A | 10/1981 | Dunning et al. |
| 4,308,872 A | 1/1982 | Watson et al. |
| 4,323,064 A | 4/1982 | Hoenig et al. |
| 4,326,513 A | 4/1982 | Schulz et al. |
| 4,391,283 A | 7/1983 | Sharpless et al. |
| 4,401,115 A | 8/1983 | Monnier |
| 4,401,116 A | 8/1983 | Fry et al. |
| 4,407,295 A | 10/1983 | Steuer et al. |
| 4,440,177 A | 4/1984 | Anderson et al. |
| 4,444,201 A | 4/1984 | Itoh |
| 4,463,764 A | 8/1984 | Anderson et al. |
| 4,473,081 A | 9/1984 | Dioguardi et al. |
| 4,495,944 A | 1/1985 | Brisson et al. |
| 4,537,190 A | 8/1985 | Caillot et al. |
| 4,550,726 A | 11/1985 | McEwen |
| 4,579,115 A | 4/1986 | Wallroth et al. |
| 4,637,385 A | 1/1987 | Rusz |
| 4,654,029 A | 3/1987 | D'Antonio |
| 4,736,750 A | 4/1988 | Valdespino et al. |
| 4,752,089 A | 6/1988 | Carter |
| 4,790,327 A | 12/1988 | Despotis |
| 4,796,639 A | 1/1989 | Snow et al. |
| 4,813,409 A | 3/1989 | Ismach |
| 4,852,582 A | 8/1989 | Pell |
| 4,867,152 A | 9/1989 | Kou et al. |
| 4,876,903 A | 10/1989 | Budinger |
| 4,878,175 A * | 10/1989 | Norden-Paul et al. ............ 705/2 |
| 4,917,108 A | 4/1990 | Mault |
| 4,921,642 A | 5/1990 | LaTorraca |
| 4,954,799 A | 9/1990 | Kumar |
| 4,984,158 A | 1/1991 | Hillsman |
| 4,990,894 A | 2/1991 | Loescher et al. |
| 5,003,985 A | 4/1991 | White et al. |
| 5,004,472 A | 4/1991 | Wallace |
| 5,009,662 A | 4/1991 | Wallace et al. |
| 5,020,527 A | 6/1991 | Dessertine |
| 5,021,046 A | 6/1991 | Wallace |
| 5,057,822 A | 10/1991 | Hoffman |
| 5,058,601 A | 10/1991 | Riker |
| 5,072,737 A | 12/1991 | Goulding |
| 5,137,026 A | 8/1992 | Waterson et al. |
| 5,150,291 A | 9/1992 | Cummings et al. |
| 5,161,525 A | 11/1992 | Kimm et al. |
| 5,163,423 A | 11/1992 | Suzuki |
| 5,167,506 A | 12/1992 | Kilis et al. |
| 5,203,343 A | 4/1993 | Axe et al. |
| 5,224,487 A | 7/1993 | Bellofatto et al. |
| 5,231,981 A | 8/1993 | Schreiber et al. |
| 5,235,973 A | 8/1993 | Levinson |
| 5,237,987 A | 8/1993 | Anderson et al. |
| 5,246,010 A | 9/1993 | Gazzara et al. |
| 5,251,632 A | 10/1993 | Delpy |
| 5,253,362 A * | 10/1993 | Nolan et al. .................... 1/1 |
| 5,261,397 A | 11/1993 | Grunstein |
| 5,261,415 A | 11/1993 | Dussault |
| 5,271,389 A | 12/1993 | Isaza et al. |
| 5,277,195 A | 1/1994 | Williams |
| 5,279,304 A | 1/1994 | Einhorn et al. |
| 5,279,549 A | 1/1994 | Ranford |
| 5,293,875 A | 3/1994 | Stone |
| 5,299,568 A | 4/1994 | Forare et al. |
| 5,301,921 A | 4/1994 | Kumar |
| 5,303,698 A | 4/1994 | Tobia et al. |
| 5,303,699 A | 4/1994 | Bonassa et al. |
| 5,307,795 A | 5/1994 | Whitwam et al. |
| 5,319,355 A | 6/1994 | Russek |
| 5,319,540 A | 6/1994 | Isaza et al. |
| 5,325,861 A | 7/1994 | Goulding |
| 5,333,106 A | 7/1994 | Lanpher et al. |
| 5,333,606 A | 8/1994 | Schneider et al. |
| 5,339,807 A | 8/1994 | Carter |
| 5,339,825 A | 8/1994 | McNaughton et al. |
| 5,343,857 A | 9/1994 | Schneider et al. |
| 5,351,522 A | 10/1994 | Lura |
| 5,355,893 A | 10/1994 | Mick et al. |
| 5,357,946 A | 10/1994 | Kee et al. |
| 5,357,975 A | 10/1994 | Kraemer et al. |
| 5,363,842 A | 11/1994 | Mishelevich et al. |
| 5,365,922 A | 11/1994 | Raemer |
| 5,368,019 A | 11/1994 | LaTorraca |
| 5,373,851 A | 12/1994 | Reinhold, Jr. et al. |
| 5,383,449 A | 1/1995 | Forare et al. |
| 5,383,470 A | 1/1995 | Kolbly |
| 5,385,142 A | 1/1995 | Brady et al. |
| 5,390,666 A | 2/1995 | Kimm et al. |
| 5,401,135 A | 3/1995 | Stoen et al. |
| 5,402,796 A | 4/1995 | Packer et al. |
| 5,404,871 A | 4/1995 | Goodman et al. |
| 5,407,174 A | 4/1995 | Kumar |
| 5,413,110 A | 5/1995 | Cummings et al. |
| 5,438,980 A | 8/1995 | Phillips |
| 5,442,940 A | 8/1995 | Secker et al. |
| 5,443,075 A | 8/1995 | Holscher |
| 5,445,160 A | 8/1995 | Culver et al. |
| 5,446,449 A | 8/1995 | Lhomer et al. |
| 5,448,996 A | 9/1995 | Bellin et al. |
| 5,452,714 A | 9/1995 | Anderson et al. |
| 5,456,264 A | 10/1995 | Series et al. |
| 5,464,410 A | 11/1995 | Skeens et al. |
| 5,479,939 A | 1/1996 | Ogino |
| 5,487,731 A | 1/1996 | Denton |
| 5,495,848 A | 3/1996 | Aylsworth et al. |
| 5,501,231 A | 3/1996 | Kaish |
| 5,507,291 A | 4/1996 | Stirbl et al. |
| 5,513,631 A | 5/1996 | McWilliams |
| 5,517,983 A | 5/1996 | Deighan et al. |
| 5,517,985 A | 5/1996 | Kirk et al. |
| 5,518,002 A | 5/1996 | Wolf et al. |
| 5,520,071 A | 5/1996 | Jones |
| 5,524,615 A | 6/1996 | Power |
| 5,531,221 A | 7/1996 | Power |
| 5,534,851 A | 7/1996 | Russek |
| 5,537,992 A | 7/1996 | Bjoernstijerna et al. |
| 5,542,410 A | 8/1996 | Goodman et al. |
| 5,542,415 A | 8/1996 | Brady |
| 5,544,674 A | 8/1996 | Kelly |
| 5,548,702 A | 8/1996 | Li et al. |
| 5,549,106 A | 8/1996 | Gruenke et al. |
| 5,549,117 A | 8/1996 | Tacklind et al. |
| 5,553,620 A | 9/1996 | Snider |
| 5,558,086 A | 9/1996 | Smith et al. |
| 5,560,353 A | 10/1996 | Willemot et al. |
| 5,564,414 A | 10/1996 | Walker et al. |
| 5,564,432 A | 10/1996 | Thomson |
| 5,571,142 A | 11/1996 | Brown et al. |
| 5,575,283 A | 11/1996 | Sjoestrand |
| 5,582,167 A | 12/1996 | Joseph |
| 5,590,648 A | 1/1997 | Mitchell et al. |
| 5,591,130 A | 1/1997 | Denton |
| 5,596,984 A | 1/1997 | O'Mahony et al. |
| 5,606,976 A | 3/1997 | Marshall |
| 5,611,335 A | 3/1997 | Makhoul et al. |
| 5,626,144 A | 5/1997 | Tacklind et al. |
| 5,630,411 A | 5/1997 | Holscher |
| 5,632,270 A | 5/1997 | O'Mahoney et al. |
| 5,632,281 A | 5/1997 | Rayburn |
| 5,634,461 A | 6/1997 | Faithfull et al. |
| 5,634,471 A | 6/1997 | Fairfax et al. |
| 5,642,735 A | 7/1997 | Kolbly |
| 5,645,048 A | 7/1997 | Brodsky et al. |
| 5,647,346 A | 7/1997 | Holscher |
| 5,651,264 A | 7/1997 | Lo et al. |
| 5,655,516 A | 8/1997 | Goodman et al. |
| 5,660,168 A | 8/1997 | Ottosson et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |

| Patent | Date | Inventor |
|---|---|---|
| 5,676,129 A | 10/1997 | Rocci, Jr. et al. |
| 5,676,132 A | 10/1997 | Tillotson et al. |
| 5,678,539 A | 10/1997 | Schubert et al. |
| 5,683,424 A | 11/1997 | Brown et al. |
| 5,692,497 A | 12/1997 | Schnitzer et al. |
| 5,697,959 A | 12/1997 | Poore |
| 5,704,346 A | 1/1998 | Inoue |
| 5,704,366 A | 1/1998 | Tacklind et al. |
| 5,704,367 A | 1/1998 | Ishikawa et al. |
| 5,706,801 A | 1/1998 | Remes et al. |
| 5,715,812 A | 2/1998 | Deighan et al. |
| 5,724,990 A | 3/1998 | Ogino |
| 5,730,140 A | 3/1998 | Fitch |
| 5,730,145 A | 3/1998 | Defares et al. |
| 5,735,287 A | 4/1998 | Thomson |
| 5,736,974 A | 4/1998 | Selker |
| 5,738,092 A | 4/1998 | Mock et al. |
| 5,740,792 A | 4/1998 | Ashley et al. |
| 5,743,267 A | 4/1998 | Nikolic et al. |
| 5,752,506 A | 5/1998 | Richardson |
| 5,752,509 A | 5/1998 | Lachmann et al. |
| 5,755,218 A | 5/1998 | Johansson et al. |
| 5,758,652 A | 6/1998 | Nikolic |
| 5,762,480 A | 6/1998 | Adahan |
| 5,771,884 A | 6/1998 | Yarnall et al. |
| 5,778,874 A | 7/1998 | Maguire et al. |
| 5,791,339 A | 8/1998 | Winter |
| 5,794,612 A | 8/1998 | Wachter et al. |
| 5,794,986 A | 8/1998 | Gansel et al. |
| 5,800,361 A | 9/1998 | Rayburn |
| 5,806,514 A | 9/1998 | Mock et al. |
| 5,809,997 A | 9/1998 | Wolf |
| 5,813,397 A | 9/1998 | Goodman et al. |
| 5,813,399 A | 9/1998 | Isaza et al. |
| 5,819,723 A | 10/1998 | Joseph |
| 5,822,715 A | 10/1998 | Worthington et al. |
| 5,826,570 A | 10/1998 | Goodman et al. |
| 5,826,575 A | 10/1998 | Lall |
| 5,827,179 A | 10/1998 | Lichter et al. |
| 5,829,441 A | 11/1998 | Kidd et al. |
| 5,839,430 A | 11/1998 | Cama |
| 5,864,938 A | 2/1999 | Gansel et al. |
| 5,865,168 A | 2/1999 | Isaza |
| 5,865,171 A | 2/1999 | Cinquin |
| 5,865,174 A | 2/1999 | Kloeppel |
| 5,875,777 A | 3/1999 | Eriksson |
| 5,878,744 A | 3/1999 | Pfeiffer |
| 5,881,717 A | 3/1999 | Isaza |
| 5,881,723 A | 3/1999 | Wallace |
| 5,884,622 A | 3/1999 | Younes |
| 5,884,623 A | 3/1999 | Winter |
| 5,891,023 A | 4/1999 | Lynn |
| 5,899,203 A | 5/1999 | Defares et al. |
| 5,909,731 A | 6/1999 | O'Mahony et al. |
| 5,915,379 A | 6/1999 | Wallace |
| 5,915,380 A | 6/1999 | Wallace |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,924,418 A | 7/1999 | Lewis |
| 5,931,160 A | 8/1999 | Gilmore |
| 5,932,812 A | 8/1999 | Delsing |
| 5,934,274 A | 8/1999 | Merrick et al. |
| 5,937,854 A | 8/1999 | Stenzler |
| 5,956,501 A | 9/1999 | Brown |
| 5,957,861 A | 9/1999 | Combs et al. |
| 5,971,937 A | 10/1999 | Ekstrom |
| 5,975,081 A | 11/1999 | Hood |
| 5,979,440 A | 11/1999 | Honkonen et al. |
| 5,980,466 A | 11/1999 | Thomson |
| 6,012,450 A | 1/2000 | Rubsamen |
| 6,017,315 A | 1/2000 | Starr |
| 6,024,089 A | 2/2000 | Wallace |
| 6,026,323 A | 2/2000 | Skladnev et al. |
| 6,032,119 A | 2/2000 | Brown et al. |
| 6,041,780 A | 3/2000 | Richard et al. |
| 6,047,860 A | 4/2000 | Sanders |
| 6,055,506 A | 4/2000 | Frasca, Jr. |
| 6,073,110 A | 6/2000 | Rhodes et al. |
| 6,076,523 A | 6/2000 | Jones et al. |
| 6,099,481 A | 8/2000 | Daniels et al. |
| 6,106,481 A | 8/2000 | Cohen |
| 6,116,240 A | 9/2000 | Merrick et al. |
| 6,116,464 A | 9/2000 | Sanders |
| 6,118,847 A | 9/2000 | Hernandez-Guerra |
| 6,119,684 A | 9/2000 | Nohl et al. |
| 6,123,073 A | 9/2000 | Schlawin et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,148,815 A | 11/2000 | Wolf |
| 6,155,257 A | 12/2000 | Lurie et al. |
| 6,158,432 A | 12/2000 | Biondi |
| 6,159,147 A | 12/2000 | Lichter et al. |
| 6,161,539 A | 12/2000 | Winter |
| 6,162,183 A | 12/2000 | Hoover |
| 6,167,362 A | 12/2000 | Brown et al. |
| 6,168,568 B1 | 1/2001 | Gavriely |
| 6,171,264 B1 | 1/2001 | Bader |
| 6,176,833 B1 | 1/2001 | Thomson |
| 6,186,956 B1 | 2/2001 | McNamee |
| 6,190,326 B1 | 2/2001 | McKinnon et al. |
| 6,192,876 B1 | 2/2001 | Denyer et al. |
| 6,198,963 B1 | 3/2001 | Haim et al. |
| 6,199,550 B1 | 3/2001 | Wiesmann et al. |
| 6,202,642 B1 | 3/2001 | McKinnon et al. |
| 6,213,955 B1 | 4/2001 | Karakasoglu et al. |
| 6,220,245 B1 | 4/2001 | Takabayashi et al. |
| 6,223,744 B1 | 5/2001 | Garon |
| 6,224,553 B1 | 5/2001 | Nevo |
| 6,233,539 B1 | 5/2001 | Brown |
| 6,234,963 B1 | 5/2001 | Blike et al. |
| 6,240,920 B1 | 6/2001 | Strom |
| 6,251,082 B1 | 6/2001 | Rayburn |
| 6,261,238 B1 | 7/2001 | Gavriely |
| 6,262,728 B1 * | 7/2001 | Alexander .............. 345/440.1 |
| 6,269,810 B1 | 8/2001 | Brooker et al. |
| 6,269,812 B1 | 8/2001 | Wallace |
| 6,273,088 B1 | 8/2001 | Hillsman |
| 6,273,444 B1 | 8/2001 | Power |
| 6,279,574 B1 | 8/2001 | Richardson et al. |
| 6,283,119 B1 | 9/2001 | Bourdon |
| 6,283,923 B1 | 9/2001 | Finkelstein et al. |
| 6,287,264 B1 | 9/2001 | Hoffman |
| 6,301,497 B1 | 10/2001 | Neustadter |
| 6,302,106 B1 | 10/2001 | Lewis |
| 6,305,373 B1 * | 10/2001 | Wallace et al. .......... 128/204.21 |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,339,410 B1 | 1/2002 | Milner |
| 6,340,348 B1 | 1/2002 | Krishnan |
| 6,342,040 B1 | 1/2002 | Starr |
| 6,349,722 B1 | 2/2002 | Gradon et al. |
| 6,349,724 B1 | 2/2002 | Burton et al. |
| 6,355,002 B1 | 3/2002 | Faram et al. |
| 6,357,438 B1 | 3/2002 | Hansen |
| 6,360,745 B1 | 3/2002 | Wallace |
| 6,362,620 B1 | 3/2002 | Debbins |
| 6,367,475 B1 | 4/2002 | Kofoed et al. |
| 6,369,838 B1 | 4/2002 | Wallace |
| 6,370,419 B1 | 4/2002 | Lampotang |
| 6,377,046 B1 | 4/2002 | Debbins |
| 6,379,301 B1 | 4/2002 | Worthington et al. |
| 6,390,088 B1 | 5/2002 | Nohl et al. |
| 6,390,091 B1 | 5/2002 | Banner et al. |
| 6,390,092 B1 | 5/2002 | Leenhoven |
| 6,390,977 B1 | 5/2002 | Faithfull et al. |
| 6,402,698 B1 | 6/2002 | Mault |
| 6,408,043 B1 | 6/2002 | Hu |
| 6,412,483 B1 | 7/2002 | Jones et al. |
| 6,415,792 B1 | 7/2002 | Schoolman |
| 6,416,471 B1 | 7/2002 | Kumar et al. |
| 6,421,650 B1 | 7/2002 | Goetz et al. |
| 6,427,687 B1 | 8/2002 | Kirk |
| 6,435,175 B1 | 8/2002 | Stenzler |
| 6,436,053 B1 | 8/2002 | Knapp, II et al. |

| Patent | Date | Name | | Patent | Date | Name |
|---|---|---|---|---|---|---|
| 6,439,229 B1 | 8/2002 | Du et al. | | 6,792,066 B1 | 9/2004 | Harder |
| 6,450,164 B1 | 9/2002 | Banner et al. | | 6,796,305 B1 | 9/2004 | Banner et al. |
| 6,454,708 B1 | 9/2002 | Ferguson et al. | | 6,801,227 B2 | 10/2004 | Bocionek |
| 6,459,933 B1 | 10/2002 | Lurie et al. | | 6,801,802 B2 | 10/2004 | Sitzman et al. |
| 6,463,930 B2 | 10/2002 | Biondi et al. | | 6,805,118 B2 | 10/2004 | Brooker et al. |
| 6,467,478 B1 | 10/2002 | Merrick et al. | | 6,807,965 B1 | 10/2004 | Hickle |
| 6,471,658 B1 | 10/2002 | Daniels et al. | | 6,814,074 B1 | 11/2004 | Nadjafizadeh et al. |
| 6,488,029 B1 | 12/2002 | Hood et al. | | 6,820,614 B2 | 11/2004 | Bonutti |
| 6,488,629 B1 | 12/2002 | Saetre | | 6,820,618 B2 | 11/2004 | Banner et al. |
| RE37,970 E | 1/2003 | Costello, Jr. | | 6,822,223 B2 | 11/2004 | Davis |
| 6,511,426 B1 | 1/2003 | Hossack | | 6,824,520 B2 | 11/2004 | Orr et al. |
| 6,512,938 B2 | 1/2003 | Claure | | 6,828,910 B2 | 12/2004 | VanRyzin et al. |
| 6,515,683 B1 | 2/2003 | Wright | | 6,830,046 B2 | 12/2004 | Blakley et al. |
| 6,517,497 B2 | 2/2003 | Rymut et al. | | 6,834,647 B2 | 12/2004 | Blair et al. |
| 6,533,723 B1 | 3/2003 | Lockery | | 6,837,242 B2 | 1/2005 | Younes |
| 6,533,730 B2 | 3/2003 | Strom | | 6,839,753 B2 | 1/2005 | Biondi |
| 6,543,449 B1 | 4/2003 | Woodring | | 6,845,773 B2 | 1/2005 | Berthon-Jones et al. |
| 6,543,701 B1 | 4/2003 | Ho | | 6,858,006 B2 | 2/2005 | MacCarter et al. |
| 6,544,192 B2 | 4/2003 | Starr | | 6,860,266 B2 | 3/2005 | Blike |
| 6,546,930 B1 | 4/2003 | Emerson et al. | | 6,866,040 B1 | 3/2005 | Bourdon |
| 6,547,728 B1 | 4/2003 | Cornuejols | | 6,866,629 B2 | 3/2005 | Bardy |
| 6,553,991 B1 | 4/2003 | Isaza | | 6,893,397 B2 | 5/2005 | Bardy |
| 6,553,992 B1 | 4/2003 | Berthon-Jones et al. | | 6,899,103 B1 | 5/2005 | Hood |
| 6,557,553 B1 | 5/2003 | Borrello | | 6,899,683 B2 | 5/2005 | Mault et al. |
| 6,557,554 B1 | 5/2003 | Sugiura | | 6,899,684 B2 | 5/2005 | Mault et al. |
| 6,566,875 B1 | 5/2003 | Hasson | | 6,910,481 B2 | 6/2005 | Kimmel et al. |
| 6,571,122 B2 | 5/2003 | Schroeppel et al. | | 6,921,369 B1 | 7/2005 | Gehrke et al. |
| 6,571,795 B2 | 6/2003 | Bourdon | | 6,923,079 B1 | 8/2005 | Snibbe |
| 6,571,796 B2 | 6/2003 | Banner et al. | | 6,931,269 B2 | 8/2005 | Terry |
| 6,578,575 B1 | 6/2003 | Jonson | | 6,932,083 B2 | 8/2005 | Jones et al. |
| 6,581,592 B1 | 6/2003 | Bathe et al. | | 6,932,767 B2 | 8/2005 | Landry |
| 6,584,973 B1 | 7/2003 | Biondi | | 6,947,780 B2 | 9/2005 | Scharf |
| 6,597,939 B1 | 7/2003 | Lampotang | | 6,951,541 B2 | 10/2005 | Desmarais |
| 6,599,252 B2 | 7/2003 | Starr | | 6,954,702 B2 | 10/2005 | Pierry et al. |
| 6,603,494 B1 | 8/2003 | Banks | | 6,956,572 B2 | 10/2005 | Zaleski |
| 6,606,993 B1 | 8/2003 | Wiesmann et al. | | 6,960,854 B2 | 11/2005 | Nadjafizadeh et al. |
| 6,620,106 B2 | 9/2003 | Mault | | 6,970,919 B1 | 11/2005 | Doi |
| 6,621,917 B1 | 9/2003 | Vilser | | 6,976,958 B2 | 12/2005 | Quy |
| 6,622,726 B1 | 9/2003 | Du | | 6,986,347 B2 | 1/2006 | Hickle |
| 6,629,934 B2 | 10/2003 | Mault et al. | | 6,997,185 B2 | 2/2006 | Han et al. |
| 6,630,176 B2 | 10/2003 | Li | | 6,997,880 B2 | 2/2006 | Carlebach et al. |
| 6,644,310 B1 | 11/2003 | Delache et al. | | 7,006,862 B2 * | 2/2006 | Kaufman et al. ............ 600/523 |
| 6,644,312 B2 | 11/2003 | Berthon-Jones et al. | | 7,008,380 B1 | 3/2006 | Rees et al. |
| 6,645,158 B1 | 11/2003 | Mault | | 7,017,574 B2 | 3/2006 | Biondi |
| 6,650,346 B1 | 11/2003 | Jaeger | | 7,019,652 B2 | 3/2006 | Richardson |
| 6,651,653 B1 | 11/2003 | Honkonen et al. | | 7,033,323 B2 | 4/2006 | Botbol et al. |
| 6,656,129 B2 | 12/2003 | Niles et al. | | 7,036,504 B2 | 5/2006 | Wallace |
| 6,668,824 B1 | 12/2003 | Isaza et al. | | 7,039,878 B2 | 5/2006 | Auer |
| 6,668,829 B2 | 12/2003 | Biondi | | 7,040,315 B1 | 5/2006 | Strömberg |
| 6,671,529 B2 | 12/2003 | Claure | | 7,040,318 B2 | 5/2006 | Däscher et al. |
| 6,673,018 B2 | 1/2004 | Friedman | | 7,040,321 B2 | 5/2006 | Göbel |
| 6,675,801 B2 | 1/2004 | Wallace | | 7,046,254 B2 | 5/2006 | Brown et al. |
| 6,679,258 B1 | 1/2004 | Strom | | 7,047,092 B2 | 5/2006 | Wimsatt |
| 6,681,764 B1 | 1/2004 | Honkonen et al. | | 7,051,736 B2 | 5/2006 | Banner et al. |
| 6,698,423 B1 | 3/2004 | Honkonen et al. | | 7,062,251 B2 | 6/2006 | Birkett |
| 6,707,476 B1 | 3/2004 | Hochstedler | | 7,066,173 B2 | 6/2006 | Banner et al. |
| 6,708,688 B1 | 3/2004 | Rubin et al. | | 7,077,125 B2 | 7/2006 | Scheuch |
| 6,709,405 B2 | 3/2004 | Jonson | | 7,077,131 B2 | 7/2006 | Hansen |
| 6,712,762 B1 | 3/2004 | Lichter et al. | | 7,081,091 B2 | 7/2006 | Merrett et al. |
| 6,718,974 B1 | 4/2004 | Moberg | | 7,081,095 B2 | 7/2006 | Lynn |
| 6,718,975 B2 | 4/2004 | Blomberg | | RE39,225 E | 8/2006 | Isaza et al. |
| 6,725,077 B1 | 4/2004 | Balloni | | 7,083,574 B2 | 8/2006 | Kline |
| 6,725,447 B1 | 4/2004 | Gilman et al. | | 7,089,927 B2 | 8/2006 | John et al. |
| 6,725,860 B2 | 4/2004 | Wallroth et al. | | 7,089,937 B2 | 8/2006 | Berthon-Jones et al. |
| 6,733,449 B1 | 5/2004 | Krishnamurthy | | 7,094,208 B2 | 8/2006 | Williams et al. |
| 6,738,079 B1 | 5/2004 | Kellerman et al. | | 7,116,810 B2 | 10/2006 | Miller et al. |
| 6,739,337 B2 | 5/2004 | Isaza | | 7,117,438 B2 | 10/2006 | Wallace |
| 6,740,046 B2 | 5/2004 | Knapp, II et al. | | 7,128,578 B2 | 10/2006 | Lampotang |
| 6,743,172 B1 | 6/2004 | Blike | | 7,137,074 B1 * | 11/2006 | Newton et al. ................ 715/835 |
| 6,744,374 B1 | 6/2004 | Kuenzner | | 7,147,600 B2 | 12/2006 | Bardy |
| 6,745,764 B2 | 6/2004 | Hickle | | 7,156,808 B2 | 1/2007 | Quy |
| 6,755,193 B2 | 6/2004 | Berthon-Jones et al. | | 7,162,296 B2 | 1/2007 | Leonhardt et al. |
| 6,755,787 B2 | 6/2004 | Hossack | | 7,164,972 B2 | 1/2007 | Imhof et al. |
| 6,760,610 B2 | 7/2004 | Tschupp et al. | | 7,165,221 B2 | 1/2007 | Monteleone |
| 6,761,167 B1 | 7/2004 | Nadjafizadeh et al. | | 7,169,112 B2 | 1/2007 | Caldwell |
| 6,761,168 B1 | 7/2004 | Nadjafizadeh et al. | | 7,172,557 B1 | 2/2007 | Parker |
| 6,776,159 B2 | 8/2004 | Pelerossi et al. | | 7,182,083 B2 | 2/2007 | Yanof et al. |
| 6,782,888 B1 | 8/2004 | Friberg | | 7,187,790 B2 | 3/2007 | Sabol |
| 6,790,178 B1 | 9/2004 | Mault et al. | | 7,188,621 B2 | 3/2007 | DeVries |

| | | | |
|---|---|---|---|
| 7,201,734 B2 | 4/2007 | Hickle | |
| 7,203,353 B2 | 4/2007 | Klotz | |
| 7,210,478 B2 | 5/2007 | Banner et al. | |
| 7,211,049 B2 | 5/2007 | Bradley et al. | |
| 7,219,666 B2 | 5/2007 | Friberg et al. | |
| 7,220,230 B2 | 5/2007 | Roteliuk et al. | |
| 7,222,054 B2 | 5/2007 | Geva | |
| 7,223,965 B2 | 5/2007 | Davis | |
| 7,228,323 B2 | 6/2007 | Angerer et al. | |
| 7,241,269 B2 | 7/2007 | McCawley et al. | |
| 7,246,618 B2 | 7/2007 | Habashi | |
| 7,247,154 B2 | 7/2007 | Hickle | |
| 7,252,640 B2 | 8/2007 | Ni et al. | |
| 7,261,690 B2 | 8/2007 | Teller et al. | |
| 7,264,730 B2 | 9/2007 | Connell | |
| 7,270,126 B2 | 9/2007 | Wallace | |
| 7,275,540 B2 | 10/2007 | Bolam et al. | |
| 7,278,579 B2 | 10/2007 | Loffredo | |
| 7,282,032 B2 | 10/2007 | Miller | |
| 7,285,090 B2 | 10/2007 | Stivoric et al. | |
| 7,294,105 B1 | 11/2007 | Islam | |
| 7,294,112 B1 | 11/2007 | Dunlop | |
| 7,298,280 B2 | 11/2007 | Voege et al. | |
| 7,300,418 B2 | 11/2007 | Zaleski | |
| 7,303,680 B2 | 12/2007 | Connel | |
| 7,308,550 B2 | 12/2007 | Cornett | |
| 7,310,551 B1 | 12/2007 | Koh et al. | |
| 7,310,720 B2 | 12/2007 | Cornett | |
| 7,311,665 B2 | 12/2007 | Hawthorne et al. | |
| 7,314,451 B2 | 1/2008 | Halperin et al. | |
| 7,316,231 B2 | 1/2008 | Hickle | |
| 7,318,808 B2 | 1/2008 | Tarassenko et al. | |
| 7,318,892 B2 | 1/2008 | Connell | |
| 7,321,802 B2 | 1/2008 | Wasner et al. | |
| 7,322,352 B2 | 1/2008 | Minshull et al. | |
| 7,322,937 B2 | 1/2008 | Blomberg et al. | |
| 7,331,340 B2 | 2/2008 | Barney | |
| 7,333,969 B2 | 2/2008 | Lee | |
| 7,334,578 B2 | 2/2008 | Biondi | |
| 7,343,916 B2 | 3/2008 | Biondo et al. | |
| 7,343,917 B2 | 3/2008 | Jones | |
| 7,347,200 B2 | 3/2008 | Jones et al. | |
| 7,347,207 B2 | 3/2008 | Ahlmen et al. | |
| 7,351,340 B2 | 4/2008 | Connell | |
| 7,362,341 B2 | 4/2008 | McGuire et al. | |
| 7,367,337 B2 | 5/2008 | Berthon-Jones et al. | |
| 7,367,955 B2 | 5/2008 | Zhang et al. | |
| 7,369,757 B2 | 5/2008 | Farbarik | |
| 7,370,650 B2 | 5/2008 | Nadjafizadeh et al. | |
| 7,374,535 B2 | 5/2008 | Schoenberg et al. | |
| 7,377,276 B2 | 5/2008 | Roy | |
| 7,380,210 B2 | 5/2008 | Lontka et al. | |
| RE40,365 E | 6/2008 | Kirchgeorg et al. | |
| 7,383,148 B2 | 6/2008 | Ahmed | |
| 7,387,610 B2 | 6/2008 | Stahmann et al. | |
| 7,413,546 B2 | 8/2008 | Agutter et al. | |
| 7,422,562 B2 | 9/2008 | Hatib et al. | |
| 7,425,201 B2 | 9/2008 | Euliano et al. | |
| 7,428,902 B2 | 9/2008 | Du et al. | |
| 7,435,220 B2 | 10/2008 | Ranucci | |
| 7,438,072 B2 | 10/2008 | Izuchukwu | |
| 7,438,073 B2 | 10/2008 | Delache et al. | |
| 7,448,383 B2 | 11/2008 | Delache et al. | |
| 7,452,333 B2 | 11/2008 | Roteliuk | |
| 7,460,959 B2 | 12/2008 | Jafari | |
| 7,464,339 B2 | 12/2008 | Keenan, Jr. et al. | |
| 7,469,698 B1 | 12/2008 | Childers et al. | |
| 7,487,773 B2 | 2/2009 | Li | |
| 7,487,774 B2 | 2/2009 | Acker | |
| 7,490,085 B2 | 2/2009 | Walker | |
| 7,496,400 B2 | 2/2009 | Hoskonen et al. | |
| 7,500,481 B2 | 3/2009 | Delache et al. | |
| 7,504,954 B2 | 3/2009 | Spaeder | |
| 7,512,450 B2 | 3/2009 | Ahmed | |
| 7,512,593 B2 | 3/2009 | Karklins et al. | |
| 7,527,053 B2 | 5/2009 | DeVries et al. | |
| 7,527,054 B2 | 5/2009 | Misholi | |
| 7,530,353 B2 | 5/2009 | Choncholas et al. | |
| RE40,806 E | 6/2009 | Gradon et al. | |
| 7,543,582 B2 | 6/2009 | Lu et al. |
| 7,548,833 B2 | 6/2009 | Ahmed |
| 7,552,731 B2 | 6/2009 | Jorczak et al. |
| 7,556,036 B2 | 7/2009 | Bouillon et al. |
| 7,559,903 B2 | 7/2009 | Moussavi et al. |
| 7,562,657 B2 | 7/2009 | Blanch et al. |
| 7,565,905 B2 | 7/2009 | Hickle |
| 7,584,712 B2 | 9/2009 | Lu |
| 7,590,551 B2 | 9/2009 | Auer |
| 7,597,099 B2 | 10/2009 | Jones et al. |
| 7,603,170 B2 | 10/2009 | Hatlestad et al. |
| 7,603,631 B2 | 10/2009 | Bermudez et al. |
| 7,606,668 B2 | 10/2009 | Pierry et al. |
| 7,609,138 B2 | 10/2009 | Dietrich et al. |
| 7,610,915 B2 | 11/2009 | Dittmann |
| 7,618,378 B2 | 11/2009 | Bingham et al. |
| 7,625,345 B2 | 12/2009 | Quinn |
| 7,630,755 B2 | 12/2009 | Stahmann et al. |
| 7,650,181 B2 | 1/2010 | Freeman et al. |
| 7,652,571 B2 | 1/2010 | Parkulo et al. |
| 7,654,802 B2 | 2/2010 | Crawford, Jr. et al. |
| 7,654,966 B2 | 2/2010 | Westinskow et al. |
| 7,658,188 B2 | 2/2010 | Halpern et al. |
| 7,662,106 B2 | 2/2010 | Daniels et al. |
| 7,668,579 B2 | 2/2010 | Lynn |
| 7,669,598 B2 | 3/2010 | Rick et al. |
| 7,671,733 B2 | 3/2010 | McNeal et al. |
| 7,678,063 B2 | 3/2010 | Felmlee et al. |
| 7,682,312 B2 | 3/2010 | Lurie |
| 7,684,931 B2 | 3/2010 | Pierry et al. |
| 7,693,697 B2 | 4/2010 | Westenskow et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,731,663 B2 | 6/2010 | Averina et al. |
| 7,736,132 B2 | 6/2010 | Bliss et al. |
| 7,740,013 B2 | 6/2010 | Ishizaki et al. |
| 7,753,049 B2 | 7/2010 | Jorczak et al. |
| 7,766,012 B2 | 8/2010 | Scheuch et al. |
| 7,771,364 B2 | 8/2010 | Arbel et al. |
| 7,772,965 B2 | 8/2010 | Farhan et al. |
| 7,778,709 B2 | 8/2010 | Gollasch et al. |
| 7,778,851 B2 | 8/2010 | Schoenberg et al. |
| 7,784,461 B2 | 8/2010 | Figueiredo et al. |
| 7,785,263 B2 | 8/2010 | Roteliuk et al. |
| 7,785,265 B2 | 8/2010 | Schätzl |
| 7,793,659 B2 | 9/2010 | Breen |
| 7,793,660 B2 | 9/2010 | Kimmel et al. |
| 7,810,497 B2 | 10/2010 | Pittman et al. |
| 7,814,906 B2 | 10/2010 | Moretti |
| 7,819,815 B2 | 10/2010 | Younes |
| 7,823,588 B2 | 11/2010 | Hansen |
| 7,831,450 B2 | 11/2010 | Schoenberg et al. |
| 7,832,394 B2 | 11/2010 | Schechter et al. |
| 7,836,882 B1 | 11/2010 | Rumph et al. |
| 7,837,629 B2 | 11/2010 | Bardy |
| 7,850,619 B2 | 12/2010 | Gavish et al. |
| 7,855,656 B2 | 12/2010 | Maschke |
| 7,855,716 B2 | 12/2010 | McCreary et al. |
| 7,859,401 B2 | 12/2010 | Falck et al. |
| 7,866,317 B2 | 1/2011 | Muellinger et al. |
| 7,871,394 B2 | 1/2011 | Halbert et al. |
| D632,796 S | 2/2011 | Ross et al. |
| D632,797 S | 2/2011 | Ross et al. |
| 7,881,780 B2 | 2/2011 | Flaherty |
| 7,883,480 B2 | 2/2011 | Dunlop |
| 7,885,828 B2 | 2/2011 | Glaser-Seidnitzer et al. |
| 7,886,231 B2 | 2/2011 | Hopermann et al. |
| 7,891,353 B2 | 2/2011 | Chalvignac |
| 7,891,354 B2 | 2/2011 | Farbarik |
| 7,893,560 B2 | 2/2011 | Carter |
| 7,895,527 B2 | 2/2011 | Zaleski et al. |
| 7,909,033 B2 | 3/2011 | Faram |
| 7,912,537 B2 | 3/2011 | Lee et al. |
| 7,927,286 B2 | 4/2011 | Ranucci |
| 7,931,601 B2 | 4/2011 | Ranucci |

| | | | |
|---|---|---|---|
| D638,852 S | 5/2011 | Skidmore et al. | |
| 7,953,419 B2 | 5/2011 | Jost et al. | |
| 7,956,719 B2 | 6/2011 | Anderson, Jr. et al. | |
| 7,958,892 B2 | 6/2011 | Kwok et al. | |
| 7,970,450 B2 | 6/2011 | Kroecker et al. | |
| 7,984,714 B2 | 7/2011 | Hausmann et al. | |
| D643,535 S | 8/2011 | Ross et al. | |
| 7,990,251 B1 | 8/2011 | Ford, Jr. | |
| 7,992,557 B2 | 8/2011 | Nadjafizadeh et al. | |
| 8,001,967 B2 | 8/2011 | Wallace et al. | |
| D645,158 S | 9/2011 | Sanchez et al. | |
| 8,021,310 B2 | 9/2011 | Sanborn et al. | |
| D649,157 S | 11/2011 | Skidmore et al. | |
| D653,749 S | 2/2012 | Winter et al. | |
| 8,113,062 B2 | 2/2012 | Graboi et al. | |
| D655,405 S | 3/2012 | Winter et al. | |
| D655,809 S | 3/2012 | Winter et al. | |
| 8,181,648 B2 | 5/2012 | Perine et al. | |
| 8,210,173 B2 | 7/2012 | Vandine | |
| 8,210,174 B2 | 7/2012 | Farbarik | |
| 8,239,780 B2 * | 8/2012 | Manetta et al. | 715/764 |
| 8,240,684 B2 | 8/2012 | Ross et al. | |
| 8,267,085 B2 | 9/2012 | Jafari et al. | |
| 8,272,379 B2 | 9/2012 | Jafari et al. | |
| 8,272,380 B2 | 9/2012 | Jafari et al. | |
| 8,302,600 B2 | 11/2012 | Andrieux et al. | |
| 8,302,602 B2 | 11/2012 | Andrieux et al. | |
| 2001/0056358 A1 | 12/2001 | Dulong | |
| 2002/0026941 A1 | 3/2002 | Biondi et al. | |
| 2002/0044059 A1 | 4/2002 | Reeder | |
| 2002/0077863 A1 | 6/2002 | Rutledge | |
| 2002/0091548 A1 | 7/2002 | Auer | |
| 2002/0171682 A1 | 11/2002 | Frank et al. | |
| 2002/0177758 A1 | 11/2002 | Schoenberg et al. | |
| 2003/0060723 A1 | 3/2003 | Joo et al. | |
| 2003/0062045 A1 * | 4/2003 | Woodring et al. | 128/204.18 |
| 2003/0106553 A1 | 6/2003 | Vanderveen | |
| 2003/0130567 A1 | 7/2003 | Mault et al. | |
| 2003/0130595 A1 | 7/2003 | Mault | |
| 2003/0140928 A1 | 7/2003 | Bui et al. | |
| 2003/0140929 A1 | 7/2003 | Wilkes et al. | |
| 2003/0141368 A1 | 7/2003 | Pascual et al. | |
| 2003/0141981 A1 | 7/2003 | Bui et al. | |
| 2003/0142138 A1 | 7/2003 | Brown et al. | |
| 2003/0144878 A1 | 7/2003 | Wilkes et al. | |
| 2003/0144880 A1 | 7/2003 | Talachian et al. | |
| 2003/0144881 A1 | 7/2003 | Talachian et al. | |
| 2003/0144882 A1 | 7/2003 | Talachian et al. | |
| 2003/0201697 A1 | 10/2003 | Richardson | |
| 2003/0204414 A1 | 10/2003 | Wilkes et al. | |
| 2003/0204416 A1 | 10/2003 | Radpay et al. | |
| 2003/0204419 A1 | 10/2003 | Wilkes et al. | |
| 2003/0204420 A1 | 10/2003 | Wilkes et al. | |
| 2003/0208152 A1 | 11/2003 | Avrahami et al. | |
| 2003/0208465 A1 | 11/2003 | Yurko | |
| 2003/0222548 A1 | 12/2003 | Richardson et al. | |
| 2003/0230308 A1 | 12/2003 | Linden | |
| 2004/0010425 A1 | 1/2004 | Wilkes et al. | |
| 2004/0021693 A1 | 2/2004 | Monteleone | |
| 2004/0034289 A1 | 2/2004 | Teller et al. | |
| 2004/0059604 A1 | 3/2004 | Zaleski | |
| 2004/0073453 A1 | 4/2004 | Nenov | |
| 2004/0078231 A1 | 4/2004 | Wilkes et al. | |
| 2004/0121767 A1 | 6/2004 | Simpson et al. | |
| 2004/0122294 A1 | 6/2004 | Hatlestad et al. | |
| 2004/0150525 A1 | 8/2004 | Wilson | |
| 2004/0167465 A1 | 8/2004 | Mihai et al. | |
| 2004/0167804 A1 | 8/2004 | Simpson et al. | |
| 2004/0172222 A1 | 9/2004 | Simpson et al. | |
| 2004/0172300 A1 | 9/2004 | Mihai et al. | |
| 2004/0172301 A1 | 9/2004 | Mihai et al. | |
| 2004/0172302 A1 | 9/2004 | Martucci et al. | |
| 2004/0176667 A1 | 9/2004 | Mihai et al. | |
| 2004/0224293 A1 | 11/2004 | Penning | |
| 2004/0236240 A1 | 11/2004 | Kraus et al. | |
| 2004/0249673 A1 | 12/2004 | Smith | |
| 2005/0016534 A1 | 1/2005 | Ost | |
| 2005/0033198 A1 | 2/2005 | Kehyayan et al. | |
| 2005/0039748 A1 | 2/2005 | Andrieux | |
| 2005/0054910 A1 | 3/2005 | Tremblay et al. | |
| 2005/0055242 A1 | 3/2005 | Bello et al. | |
| 2005/0055244 A1 | 3/2005 | Mullan et al. | |
| 2005/0065817 A1 | 3/2005 | Mihai et al. | |
| 2005/0075542 A1 | 4/2005 | Goldreich | |
| 2005/0075904 A1 | 4/2005 | Wager | |
| 2005/0085869 A1 | 4/2005 | Tehrani | |
| 2005/0104860 A1 | 5/2005 | McCreary | |
| 2005/0108057 A1 | 5/2005 | Cohen | |
| 2005/0112013 A1 | 5/2005 | DeVries et al. | |
| 2005/0112325 A1 | 5/2005 | Hickle | |
| 2005/0124866 A1 | 6/2005 | Elaz | |
| 2005/0133027 A1 | 6/2005 | Elaz | |
| 2005/0137480 A1 | 6/2005 | Alt et al. | |
| 2005/0139212 A1 | 6/2005 | Bourdon | |
| 2005/0139213 A1 | 6/2005 | Blike | |
| 2005/0143632 A1 | 6/2005 | Elaz | |
| 2005/0156933 A1 | 7/2005 | Lee et al. | |
| 2005/0171876 A1 | 8/2005 | Golden | |
| 2005/0177096 A1 | 8/2005 | Bollish et al. | |
| 2005/0188083 A1 * | 8/2005 | Biondi et al. | 709/224 |
| 2005/0192488 A1 | 9/2005 | Bryenton et al. | |
| 2005/0204310 A1 | 9/2005 | De Zwart et al. | |
| 2005/0215904 A1 | 9/2005 | Sumanaweera | |
| 2005/0217674 A1 | 10/2005 | Burton et al. | |
| 2005/0251040 A1 | 11/2005 | Relkuntwar | |
| 2005/0288571 A1 | 12/2005 | Perkins | |
| 2006/0047202 A1 | 3/2006 | Elliott | |
| 2006/0078867 A1 | 4/2006 | Penny et al. | |
| 2006/0080140 A1 | 4/2006 | Buttner | |
| 2006/0080343 A1 | 4/2006 | Carter | |
| 2006/0102171 A1 | 5/2006 | Gavish | |
| 2006/0122474 A1 | 6/2006 | Teller et al. | |
| 2006/0129055 A1 | 6/2006 | Orr et al. | |
| 2006/0144396 A1 | 7/2006 | DeVries | |
| 2006/0149144 A1 | 7/2006 | Lynn et al. | |
| 2006/0149589 A1 | 7/2006 | Wager | |
| 2006/0150982 A1 | 7/2006 | Wood | |
| 2006/0155183 A1 | 7/2006 | Kroecker | |
| 2006/0155206 A1 | 7/2006 | Lynn | |
| 2006/0155207 A1 | 7/2006 | Lynn et al. | |
| 2006/0161071 A1 | 7/2006 | Lynn et al. | |
| 2006/0173257 A1 | 8/2006 | Nagai et al. | |
| 2006/0174884 A1 | 8/2006 | Habashi | |
| 2006/0178911 A1 | 8/2006 | Syed et al. | |
| 2006/0189880 A1 | 8/2006 | Lynn et al. | |
| 2006/0189900 A1 | 8/2006 | Flaherty | |
| 2006/0195041 A1 | 8/2006 | Lynn | |
| 2006/0196507 A1 | 9/2006 | Bradley | |
| 2006/0200009 A1 | 9/2006 | Wekell et al. | |
| 2006/0213518 A1 | 9/2006 | DeVries | |
| 2006/0229822 A1 | 10/2006 | Theobald | |
| 2006/0235324 A1 | 10/2006 | Lynn | |
| 2006/0237015 A1 | 10/2006 | Berthon-Jones et al. | |
| 2006/0249151 A1 | 11/2006 | Gambone | |
| 2006/0249153 A1 | 11/2006 | DeVries et al. | |
| 2006/0264762 A1 | 11/2006 | Starr | |
| 2006/0278221 A1 | 12/2006 | Schermeier et al. | |
| 2006/0278222 A1 | 12/2006 | Schermeier et al. | |
| 2006/0293609 A1 | 12/2006 | Stahmann et al. | |
| 2006/0294464 A1 | 12/2006 | Tokimoto et al. | |
| 2007/0000490 A1 | 1/2007 | DeVries | |
| 2007/0000494 A1 | 1/2007 | Banner et al. | |
| 2007/0016441 A1 | 1/2007 | Stroup | |
| 2007/0017515 A1 | 1/2007 | Wallace | |
| 2007/0021673 A1 | 1/2007 | Arbel et al. | |
| 2007/0028921 A1 | 2/2007 | Banner et al. | |
| 2007/0038081 A1 | 2/2007 | Eck et al. | |
| 2007/0060812 A1 | 3/2007 | Harel et al. | |
| 2007/0062532 A1 | 3/2007 | Choncholas | |
| 2007/0062533 A1 | 3/2007 | Choncholas et al. | |
| 2007/0073181 A1 | 3/2007 | Pu | |
| 2007/0077200 A1 | 4/2007 | Baker | |
| 2007/0113849 A1 | 5/2007 | Matthews | |
| 2007/0119453 A1 | 5/2007 | Lu et al. | |
| 2007/0123758 A1 | 5/2007 | Miesel et al. | |
| 2007/0123792 A1 | 5/2007 | Kline | |
| 2007/0129647 A1 | 6/2007 | Lynn | |
| 2007/0149860 A1 | 6/2007 | Lynn et al. | |

| | | | | | | |
|---|---|---|---|---|---|---|
| 2007/0156060 A1 | 7/2007 | Cervantes | | 2008/0312954 A1 | 12/2008 | Ullrich |
| 2007/0156456 A1 | 7/2007 | McGillin | | 2008/0319513 A1 | 12/2008 | Pu |
| 2007/0157931 A1 | 7/2007 | Parker | | 2009/0005651 A1 | 1/2009 | Ward |
| 2007/0163589 A1 | 7/2007 | DeVries | | 2009/0007909 A1 | 1/2009 | Carrico |
| 2007/0179357 A1 | 8/2007 | Bardy | | 2009/0038921 A1 | 2/2009 | Kaps et al. |
| 2007/0185390 A1 | 8/2007 | Perkins et al. | | 2009/0054743 A1 | 2/2009 | Stewart |
| 2007/0191697 A1 | 8/2007 | Lynn et al. | | 2009/0055735 A1 | 2/2009 | Zaleski |
| 2007/0199566 A1 | 8/2007 | Be'eri | | 2009/0062725 A1 | 3/2009 | Goebel |
| 2007/0208438 A1 | 9/2007 | El-Mankabady et al. | | 2009/0063181 A1 | 3/2009 | Nho |
| 2007/0215155 A1 | 9/2007 | Marx et al. | | 2009/0065004 A1 | 3/2009 | Childers et al. |
| 2007/0225574 A1 | 9/2007 | Ueda | | 2009/0076342 A1 | 3/2009 | Amurthur et al. |
| 2007/0227537 A1 | 10/2007 | Bemister et al. | | 2009/0124917 A1 | 5/2009 | Hatlestad et al. |
| 2007/0229249 A1 | 10/2007 | McNeal | | 2009/0125333 A1 | 5/2009 | Heywood |
| 2007/0241884 A1 | 10/2007 | Yamazaki | | 2009/0126734 A1 | 5/2009 | Dunsmore |
| 2007/0265510 A1 | 11/2007 | Bardy | | 2009/0131758 A1 | 5/2009 | Heywood |
| 2007/0265877 A1 | 11/2007 | Rice et al. | | 2009/0133701 A1 | 5/2009 | Brain |
| 2007/0271122 A1 | 11/2007 | Zaleski | | 2009/0143694 A1 | 6/2009 | Krauss et al. |
| 2007/0272241 A1 | 11/2007 | Sanborn | | 2009/0145438 A1 | 6/2009 | Brain |
| 2007/0272242 A1 | 11/2007 | Sanborn | | 2009/0149200 A1 | 6/2009 | Jayasinghe |
| 2007/0273216 A1 | 11/2007 | Farbarik | | 2009/0149723 A1 | 6/2009 | Krauss et al. |
| 2007/0276439 A1 | 11/2007 | Miesel et al. | | 2009/0149743 A1 | 6/2009 | Barron et al. |
| 2007/0284361 A1 | 12/2007 | Nadjafizadeh et al. | | 2009/0149927 A1 | 6/2009 | Kneuer |
| 2007/0293741 A1 | 12/2007 | Bardy | | 2009/0150184 A1 | 6/2009 | Spahn |
| 2008/0000477 A1 | 1/2008 | Huster et al. | | 2009/0165795 A1 | 7/2009 | Nadjafizadeh et al. |
| 2008/0000479 A1 | 1/2008 | Elaz | | 2009/0171167 A1 | 7/2009 | Baker, Jr. |
| 2008/0007396 A1 | 1/2008 | Parkulo | | 2009/0171176 A1 | 7/2009 | Andersohn |
| 2008/0022215 A1* | 1/2008 | Lee et al. .................. 715/762 | | 2009/0192421 A1 | 7/2009 | Huster et al. |
| 2008/0033661 A1 | 2/2008 | Syroid et al. | | 2009/0205661 A1 | 8/2009 | Stephenson et al. |
| 2008/0039735 A1 | 2/2008 | Hickerson | | 2009/0205663 A1 | 8/2009 | Vandine et al. |
| 2008/0041380 A1 | 2/2008 | Wallace | | 2009/0209828 A1 | 8/2009 | Musin |
| 2008/0045844 A1 | 2/2008 | Arbel et al. | | 2009/0209849 A1 | 8/2009 | Rowe |
| 2008/0047554 A1 | 2/2008 | Roy | | 2009/0216145 A1 | 8/2009 | Skerl et al. |
| 2008/0053438 A1 | 3/2008 | DeVries | | 2009/0221926 A1 | 9/2009 | Younes |
| 2008/0053441 A1 | 3/2008 | Gottlib et al. | | 2009/0240523 A1 | 9/2009 | Friedlander |
| 2008/0064963 A1 | 3/2008 | Schwaibold et al. | | 2009/0241952 A1 | 10/2009 | Nicolazzi |
| 2008/0065420 A1 | 3/2008 | Tirinato | | 2009/0241953 A1 | 10/2009 | Vandine et al. |
| 2008/0066753 A1 | 3/2008 | Martin et al. | | 2009/0241956 A1 | 10/2009 | Baker, Jr. |
| 2008/0072896 A1 | 3/2008 | Setzer | | 2009/0241957 A1 | 10/2009 | Baker, Jr. |
| 2008/0072900 A1 | 3/2008 | Kenyon et al. | | 2009/0241958 A1 | 10/2009 | Baker, Jr. |
| 2008/0072901 A1 | 3/2008 | Habashi | | 2009/0241962 A1 | 10/2009 | Jafari et al. |
| 2008/0072902 A1 | 3/2008 | Setzer | | 2009/0244003 A1 | 10/2009 | Bonnat |
| 2008/0076970 A1 | 3/2008 | Foulis et al. | | 2009/0247891 A1 | 10/2009 | Wood |
| 2008/0077033 A1 | 3/2008 | Figueiredo | | 2009/0249247 A1* | 10/2009 | Tseng et al. .................. 715/808 |
| 2008/0077038 A1 | 3/2008 | McDonough et al. | | 2009/0250054 A1 | 10/2009 | Loncar |
| 2008/0077436 A1 | 3/2008 | Muradia | | 2009/0301486 A1 | 12/2009 | Masic |
| 2008/0078390 A1 | 4/2008 | Milne | | 2009/0301487 A1 | 12/2009 | Masic |
| 2008/0083644 A1 | 4/2008 | Janbakhsh et al. | | 2009/0301490 A1 | 12/2009 | Masic |
| 2008/0086691 A1 | 4/2008 | Hopermann et al. | | 2009/0301491 A1 | 12/2009 | Masic et al. |
| 2008/0091122 A1 | 4/2008 | Dunlop | | 2010/0004517 A1 | 1/2010 | Bryenton et al. |
| 2008/0092043 A1 | 4/2008 | Trethewey | | 2010/0011307 A1 | 1/2010 | Desfossez et al. |
| 2008/0092894 A1 | 4/2008 | Nicolazzi et al. | | 2010/0022904 A1 | 1/2010 | Centen |
| 2008/0097234 A1 | 4/2008 | Nicolazzi et al. | | 2010/0024820 A1 | 2/2010 | Bourdon |
| 2008/0103368 A1 | 5/2008 | Craine et al. | | 2010/0030092 A1 | 2/2010 | Kristensen et al. |
| 2008/0110460 A1 | 5/2008 | Elaz | | 2010/0048985 A1 | 2/2010 | Henke et al. |
| 2008/0125873 A1 | 5/2008 | Payne | | 2010/0048986 A1 | 2/2010 | Henke et al. |
| 2008/0154100 A1 | 6/2008 | Thalmeier et al. | | 2010/0049034 A1 | 2/2010 | Eck et al. |
| 2008/0161653 A1 | 7/2008 | Lin et al. | | 2010/0049264 A1 | 2/2010 | Henke et al. |
| 2008/0172249 A1 | 7/2008 | Glaser-Seidnitzer | | 2010/0049265 A1 | 2/2010 | Henke et al. |
| 2008/0178880 A1 | 7/2008 | Christopher | | 2010/0051026 A1 | 3/2010 | Graboi |
| 2008/0178882 A1 | 7/2008 | Christopher | | 2010/0051029 A1 | 3/2010 | Jafari et al. |
| 2008/0183057 A1 | 7/2008 | Taube | | 2010/0056852 A1 | 3/2010 | Henke et al. |
| 2008/0185009 A1 | 8/2008 | Choncholas | | 2010/0056853 A1 | 3/2010 | Henke et al. |
| 2008/0205427 A1 | 8/2008 | Jost | | 2010/0056855 A1 | 3/2010 | Henke et al. |
| 2008/0208012 A1 | 8/2008 | Ali | | 2010/0056929 A1 | 3/2010 | Stahmann et al. |
| 2008/0214947 A1 | 9/2008 | Hunt | | 2010/0056941 A1 | 3/2010 | Henke et al. |
| 2008/0230057 A1 | 9/2008 | Sutherland | | 2010/0056942 A1 | 3/2010 | Henke et al. |
| 2008/0236582 A1 | 10/2008 | Tehrani | | 2010/0057148 A1 | 3/2010 | Henke et al. |
| 2008/0236585 A1 | 10/2008 | Parker | | 2010/0059061 A1 | 3/2010 | Brain |
| 2008/0243016 A1 | 10/2008 | Liao et al. | | 2010/0063348 A1 | 3/2010 | Henke et al. |
| 2008/0251070 A1 | 10/2008 | Pinskiy | | 2010/0063350 A1 | 3/2010 | Henke et al. |
| 2008/0255880 A1 | 10/2008 | Beller | | 2010/0063365 A1 | 3/2010 | Pisani et al. |
| 2008/0258929 A1 | 10/2008 | Maschke | | 2010/0069761 A1 | 3/2010 | Karst et al. |
| 2008/0270912 A1 | 10/2008 | Booth | | 2010/0069774 A1 | 3/2010 | Bingham et al. |
| 2008/0281219 A1 | 11/2008 | Glickman et al. | | 2010/0071689 A1 | 3/2010 | Thiessen |
| 2008/0293025 A1 | 11/2008 | Zamierowsi et al. | | 2010/0071692 A1 | 3/2010 | Porges |
| 2008/0295830 A1 | 12/2008 | Martonen | | 2010/0071695 A1 | 3/2010 | Thiessen |
| 2008/0295839 A1 | 12/2008 | Habashi | | 2010/0071696 A1 | 3/2010 | Jafari |
| 2008/0306351 A1 | 12/2008 | Izumi | | 2010/0071697 A1 | 3/2010 | Jafari et al. |
| 2008/0308109 A1 | 12/2008 | Brain | | 2010/0072055 A1 | 3/2010 | Tanaka et al. |

| | | | | | | |
|---|---|---|---|---|---|---|
| 2010/0076278 A1 | 3/2010 | van der Zande et al. | | 2012/0000469 A1 | 1/2012 | Milne et al. |
| 2010/0078017 A1 | 4/2010 | Andrieux et al. | | 2012/0000470 A1 | 1/2012 | Milne et al. |
| 2010/0078026 A1 | 4/2010 | Andrieux et al. | | 2012/0029317 A1 | 2/2012 | Doyle et al. |
| 2010/0081119 A1 | 4/2010 | Jafari et al. | | 2012/0030611 A1 | 2/2012 | Skidmore |
| 2010/0081890 A1 | 4/2010 | Li et al. | | 2012/0060841 A1 | 3/2012 | Crawford, Jr. et al. |
| 2010/0081955 A1 | 4/2010 | Wood, Jr. et al. | | 2012/0066609 A1 | 3/2012 | Howard et al. |
| 2010/0083968 A1 | 4/2010 | Wondka et al. | | 2012/0071729 A1 | 3/2012 | Doyle et al. |
| 2010/0095961 A1 | 4/2010 | Tornesel et al. | | 2012/0090611 A1 | 4/2012 | Graboi et al. |
| 2010/0130873 A1 | 5/2010 | Yuen et al. | | 2012/0096381 A1 | 4/2012 | Milne et al. |
| 2010/0139660 A1 | 6/2010 | Adahan | | 2012/0133519 A1 | 5/2012 | Milne et al. |
| 2010/0147303 A1 | 6/2010 | Jafari et al. | | 2012/0136222 A1 | 5/2012 | Doyle et al. |
| 2010/0160839 A1 | 6/2010 | Freeman et al. | | 2012/0137249 A1 | 5/2012 | Milne et al. |
| 2010/0186744 A1 | 7/2010 | Andrieux | | 2012/0137250 A1 | 5/2012 | Milne et al. |
| 2010/0218765 A1 | 9/2010 | Jafari et al. | | | | |
| 2010/0218766 A1 | 9/2010 | Milne | | FOREIGN PATENT DOCUMENTS | | |
| 2010/0218767 A1 | 9/2010 | Jafari et al. | | | | |
| 2010/0236555 A1 | 9/2010 | Jafari et al. | | EP | 1421966 | 5/2004 |
| 2010/0242961 A1 | 9/2010 | Mougel et al. | | EP | 1464357 | 10/2004 |
| 2010/0274100 A1 | 10/2010 | Behar et al. | | GB | 2319967 | 6/1998 |
| 2010/0282259 A1 | 11/2010 | Figueiredo et al. | | WO | WO9014852 A1 | 12/1990 |
| 2010/0288283 A1 | 11/2010 | Campbell et al. | | WO | WO9308534 A1 | 4/1993 |
| 2010/0298718 A1 | 11/2010 | Gilham et al. | | WO | WO9312823 A2 | 7/1993 |
| 2010/0300446 A1 | 12/2010 | Nicolazzi et al. | | WO | WO9314696 A1 | 8/1993 |
| 2010/0312132 A1 | 12/2010 | Wood et al. | | WO | WO9414374 A1 | 7/1994 |
| 2010/0317980 A1 | 12/2010 | Guglielmino | | WO | WO9508471 A1 | 3/1995 |
| 2011/0004489 A1 | 1/2011 | Schoenberg et al. | | WO | WO9532480 A1 | 11/1995 |
| 2011/0009746 A1 | 1/2011 | Tran et al. | | WO | WO9624285 A1 | 8/1996 |
| 2011/0011400 A1 | 1/2011 | Gentner et al. | | WO | WO9720592 A1 | 6/1997 |
| 2011/0015493 A1 | 1/2011 | Koschek | | WO | WO9811840 A1 | 3/1998 |
| 2011/0023878 A1 | 2/2011 | Thiessen | | WO | WO9814116 A2 | 4/1998 |
| 2011/0023879 A1 | 2/2011 | Vandine et al. | | WO | WO9829790 A2 | 7/1998 |
| 2011/0023880 A1 | 2/2011 | Thiessen | | WO | WO9833554 A1 | 8/1998 |
| 2011/0023881 A1 | 2/2011 | Thiessen | | WO | 9841267 | 9/1998 |
| 2011/0029910 A1 | 2/2011 | Thiessen | | WO | WO9840014 A1 | 9/1998 |
| 2011/0041849 A1 | 2/2011 | Chen et al. | | WO | WO9841267 C1 | 9/1998 |
| 2011/0041850 A1 | 2/2011 | Vandine et al. | | WO | WO9841269 A1 | 9/1998 |
| 2011/0054289 A1 | 3/2011 | Derchak et al. | | WO | WO9841270 A1 | 9/1998 |
| 2011/0055720 A1 | 3/2011 | Potter et al. | | WO | WO9841271 A1 | 9/1998 |
| 2011/0098638 A1 | 4/2011 | Chawla et al. | | WO | WO9858219 A1 | 12/1998 |
| 2011/0126151 A1* | 5/2011 | Bean et al. ................... 715/810 | | WO | WO9903524 A1 | 1/1999 |
| 2011/0126829 A1 | 6/2011 | Carter et al. | | WO | WO9952431 A1 | 10/1999 |
| 2011/0126832 A1 | 6/2011 | Winter et al. | | WO | WO9952437 A1 | 10/1999 |
| 2011/0126834 A1 | 6/2011 | Winter et al. | | WO | WO9959460 A2 | 11/1999 |
| 2011/0126835 A1 | 6/2011 | Winter et al. | | WO | WO9962403 A1 | 12/1999 |
| 2011/0126836 A1 | 6/2011 | Winter et al. | | WO | WO0018293 A1 | 4/2000 |
| 2011/0126837 A1 | 6/2011 | Winter et al. | | WO | WO0019886 A1 | 4/2000 |
| 2011/0128008 A1 | 6/2011 | Carter | | WO | WO0062664 A1 | 10/2000 |
| 2011/0132361 A1 | 6/2011 | Sanchez | | WO | WO0100264 A1 | 1/2001 |
| 2011/0132362 A1 | 6/2011 | Sanchez | | WO | WO0100265 A1 | 1/2001 |
| 2011/0132364 A1 | 6/2011 | Ogilvie et al. | | WO | WO0128416 A1 | 4/2001 |
| 2011/0132365 A1 | 6/2011 | Patel et al. | | WO | WO0134022 A1 | 5/2001 |
| 2011/0132366 A1 | 6/2011 | Ogilvie et al. | | WO | WO0245566 A2 | 6/2002 |
| 2011/0132367 A1 | 6/2011 | Patel | | WO | WO02082967 A2 | 10/2002 |
| 2011/0132368 A1 | 6/2011 | Sanchez et al. | | WO | WO03015005 A2 | 2/2003 |
| 2011/0132369 A1 | 6/2011 | Sanchez | | WO | WO03024317 A2 | 3/2003 |
| 2011/0132371 A1 | 6/2011 | Sanchez et al. | | WO | WO03045493 A2 | 6/2003 |
| 2011/0133936 A1 | 6/2011 | Sanchez et al. | | WO | WO03053503 A1 | 7/2003 |
| 2011/0138308 A1 | 6/2011 | Palmer et al. | | WO | WO03060650 A2 | 7/2003 |
| 2011/0138309 A1 | 6/2011 | Skidmore et al. | | WO | WO03060651 A2 | 7/2003 |
| 2011/0138311 A1 | 6/2011 | Palmer | | WO | WO03075989 A2 | 9/2003 |
| 2011/0138315 A1 | 6/2011 | Vandine et al. | | WO | WO03075990 A2 | 9/2003 |
| 2011/0138323 A1 | 6/2011 | Skidmore et al. | | WO | WO03075991 A1 | 9/2003 |
| 2011/0146681 A1 | 6/2011 | Jafari et al. | | WO | WO03084405 A2 | 10/2003 |
| 2011/0146683 A1 | 6/2011 | Jafari et al. | | WO | WO2004014216 A2 | 2/2004 |
| 2011/0154241 A1 | 6/2011 | Skidmore et al. | | WO | WO2004014226 A1 | 2/2004 |
| 2011/0175728 A1 | 7/2011 | Baker, Jr. | | WO | WO2004032719 A2 | 4/2004 |
| 2011/0196251 A1 | 8/2011 | Jourdain et al. | | WO | WO2004043254 A1 | 5/2004 |
| 2011/0209702 A1 | 9/2011 | Vuong et al. | | WO | WO2005010796 | 2/2005 |
| 2011/0209704 A1 | 9/2011 | Jafari et al. | | WO | WO2005024729 A1 | 3/2005 |
| 2011/0209707 A1 | 9/2011 | Terhark | | WO | WO2005055825 A1 | 6/2005 |
| 2011/0213215 A1 | 9/2011 | Doyle et al. | | WO | WO2005056087 A1 | 6/2005 |
| 2011/0259330 A1 | 10/2011 | Jafari et al. | | WO | WO2005069740 A2 | 8/2005 |
| 2011/0259332 A1 | 10/2011 | Sanchez et al. | | WO | WO2005077260 A1 | 8/2005 |
| 2011/0259333 A1 | 10/2011 | Sanchez et al. | | WO | WO2005112739 A1 | 12/2005 |
| 2011/0265024 A1 | 10/2011 | Leone et al. | | WO | WO2006008745 A2 | 1/2006 |
| 2011/0271960 A1 | 11/2011 | Milne et al. | | WO | WO2006009830 A2 | 1/2006 |
| 2011/0273299 A1 | 11/2011 | Milne et al. | | WO | WO2006037184 A1 | 4/2006 |
| 2012/0000467 A1 | 1/2012 | Milne et al. | | WO | WO2006050388 A2 | 5/2006 |
| 2012/0000468 A1 | 1/2012 | Milne et al. | | WO | WO2006051466 A1 | 5/2006 |
| | | | | WO | WO2006078432 A2 | 7/2006 |

| | | | |
|---|---|---|---|
| WO | WO2006094055 A2 | 9/2006 |
| WO | WO2006096080 A1 | 9/2006 |
| WO | WO2006109072 A2 | 10/2006 |
| WO | WO2006123956 A1 | 11/2006 |
| WO | WO2006125986 A1 | 11/2006 |
| WO | WO2006125987 A1 | 11/2006 |
| WO | WO2006125989 A1 | 11/2006 |
| WO | WO2006125990 A1 | 11/2006 |
| WO | WO2006137067 A2 | 12/2006 |
| WO | WO2007033050 A2 | 3/2007 |
| WO | WO2007106804 A2 | 9/2007 |
| WO | WO2007145948 | 12/2007 |
| WO | WO2008030091 A1 | 3/2008 |
| WO | WO2008042699 A2 | 4/2008 |
| WO | WO2008058997 A2 | 5/2008 |
| WO | WO2008062554 A1 | 5/2008 |
| WO | WO2008113410 A1 | 9/2008 |
| WO | WO2008118951 A1 | 10/2008 |
| WO | WO2008140528 A1 | 11/2008 |
| WO | WO2008146264 A2 | 12/2008 |
| WO | WO2008148134 A1 | 12/2008 |
| WO | WO2009024967 A2 | 2/2009 |
| WO | WO2009027864 A1 | 3/2009 |
| WO | WO2009036334 A1 | 3/2009 |
| WO | WO2009124297 A1 | 10/2009 |
| WO | WO2010009531 A1 | 1/2010 |
| WO | WO2010020980 A1 | 2/2010 |
| WO | WO2010021730 A1 | 2/2010 |
| WO | WO2010039989 A1 | 4/2010 |
| WO | WO2010126916 A1 | 11/2010 |
| WO | WO2010141415 A1 | 12/2010 |
| WO | WO2011005953 A2 | 1/2011 |
| WO | WO2011022242 A1 | 2/2011 |

OTHER PUBLICATIONS

PCT International Search Report and Written Opinion in Application PCT/US2010/058131, mailed May 18, 2011, 12 pgs.
PCT International Search Report and Written Opinion in Application PCT/US2010/058132, mailed Mar. 3, 2011, 10 pgs.
U.S. Appl. No. 12/631,685, Office Action mailed Nov. 15, 2011, 22 pgs.
U.S. Appl. No. 12/631,685, Office Action mailed Feb. 29, 2012, 23 pgs.
U.S. Appl. No. 12/631,712, Office Action mailed Nov. 14, 2011, 20 pgs.
U.S. Appl. No. 12/631,712, Office Action mailed Feb. 29, 2012, 22 pgs.
U.S. Appl. No. 12/631,750, Office Action mailed Dec. 8, 2011, 12 pgs.
U.S. Appl. No. 12/631,752, Office Action mailed Dec. 8, 2011, 12 pgs.
U.S. Appl. No. 12/760,649, Office Action mailed Jan. 6, 2012, 11 pgs.
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operators and Technical Reference Manual. Series Ventilator System, Nellcor Puritan Bennett, Part No. 4-070088-00, Rev. L, Aug. 2010, pp. 1-476.
840 Operators and Technical Reference Manual. Ventilator System, Nellcor Puritan Bennett, Part No. 4-075609-00, Rev. G, Oct. 2006, pp. 1-424.
PCT International Search Report mailed Apr. 7, 2011, Applicant's Reference H-RM-01984WO, International Application No. PCT/US2010/060871, International Filing Date Dec. 16, 2010, Applicant Nellcor Puritan Bennett LLC, 3 pages.
U.S. Appl. No. 12/631,685, Advisory Action mailed May 11, 2012, 3 pgs.
U.S. Appl. No. 12/631,712, Advisory Action mailed May 11, 2012, 3 pgs.
U.S. Appl. No. 12/631,750, Advisory Action mailed Jul. 24, 2012, 3 pgs.
U.S. Appl. No. 12/631,750, Office Action mailed May 16, 2012, 13 pgs.
U.S. Appl. No. 12/631,752, Notice of Allowance mailed Jun. 11, 2012, 8 pgs.
U.S. Appl. No. 12/631,752, Notice of Allowance mailed Jul. 24, 2012, 8 pgs.
U.S. Appl. No. 12/631,752, Office Action mailed Mar. 15, 2012, 13 pgs.
U.S. Appl. No. 12/760,649, Office Action mailed Jul. 20, 2012, 13 pgs.
U.S. Appl. No. 12/631,750, Office Action mailed Oct. 4, 2012, 13 pgs.
U.S. Appl. No. 12/844,579, Office Action mailed Aug. 30, 2012, 9 pgs.
U.S. Appl. No. 12/844,579, Office Action mailed Dec. 19, 2012, 8 pgs.
U.S. Appl. No. 12/760,649, Advisory Action mailed Sep. 28, 2012, 3 pgs.
U.S. Appl. No. 12/844,579, Advisory Action mailed Feb. 14, 2013, 3 pgs.
US 7,284,551, 10/2007, Jones et al. (withdrawn)

* cited by examiner

VISUAL INDICATION OF ALARMS ON A VENTILATOR GRAPHICAL USER INTERFACE

RELATED APPLICATIONS

This application claims benefit under 35 U.S.C. §119(e) to U.S. Provisional Application No. 61/287,914 entitled "Graphical User Interface for Use on Medical Ventilator" filed on Dec. 18, 2009 the entire disclosure of all of which is hereby incorporated herein by reference.

INTRODUCTION

A ventilator is a device that mechanically helps patients breathe by replacing some or all of the muscular effort required to inflate and deflate the lungs. During ventilation, the ventilator may be configured to generate various alarms upon detecting a change in the patient's condition, a malfunction of the ventilatory equipment, or other indication that clinician intervention may be warranted. Thus, alarms generally function to alert a clinician of an abnormal or unsafe condition that may impact the patient. In this sense, alarms are a very important and necessary feature of any therapeutic instrument. However, alarms may not convey enough information regarding which alarms need to be alleviated first. In addition, multiple simultaneous alarms may compound this insufficiency of alarm information, costing the clinician valuable time while deciding which alarm to address first.

Visual Indication of Alarms on a Ventilator Graphical User Interface

The disclosure describes improved systems and methods for displaying alarms to a clinician in a ventilatory system. Specifically, embodiments described herein seek to optimize the informative presentation of alarms on a ventilator interface. Embodiments of the present disclosure may provide one or more selection elements, each selection element indicating a summarized alarm message. The summarized alarm message may include a parameter indication, an alarm event indication, and an alarm level indication. The one or more summarized alarm messages are associated with ranked alarm events. The most highly ranked alarm event is displayed in a selection element at the top of a hierarchical display, with the next most highly ranked alarm event displayed below it in descending order of rank. An alarm event's ranking is determined, first by the alarm level. In some embodiments, alarm events are associated with high, medium or low alarm levels. If an alarm event is the only alarm event associated with a high alarm level, it will be ranked highest and displayed in the selection element at the top of the hierarchical display. However, if two alarm events are both associated with a high alarm level, a ranking determination is made by comparing the parameter priority associated with each alarm event. Each ventilatory parameter is assigned a priority level. In the case of identical alarm levels, the alarm event associated with the parameter with the highest parameter priority will be ranked higher.

Alarm event rankings can change over time. For example, an alarm level for a given alarm event can elevate or de-elevate, depending on the condition of the patient. When an alarm event's ranking changes, the hierarchical display of alarm events is rearranged to reflect the new ranking. As will be appreciated, all alarm events, such as an alarm event with a low ranking, may not be provided in the graphical display. As a result, if an alarm event's ranking drops enough, it may disappear from the graphical display completely and a new alarm event may replace it. In some embodiments, the rearrangement is displayed by "floating" the alarm messages either up or down the hierarchical display based on whether the ranking has increased or decreased.

Other embodiments of the present disclosure provide for an expanded alarm message. Upon accessing a selection element in the hierarchical display, a clinician can ascertain more information about the alarm event including, but not limited to, suggested alarm alleviation measures, detailed alarm event description, and a hyperlink to an alarm settings window. In one embodiment, a clinician can access the hyperlink to access an alarm settings window providing more information about all the alarms. As discussed above, the graphical display may not display all currently emitting alarms. The alarm settings window provides the clinician with information about all currently emitting alarms with user adjustable parameters. The alarm settings window may also provide the clinician with an opportunity to adjust alarm settings for each ventilatory parameter.

Other embodiments of the present disclosure provide for an alarm log window. The alarm log window provides a clinician with a temporal log of all alarm events. In one embodiment, the alarm log window records all alarm events since manual reset of the ventilator. In another embodiment, the alarm log window records all alarm events since the ventilator began monitoring a new patient.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which from a part of this application, are illustrative of described technology and are not meant to limit the scope of the invention as claimed in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment having user interfaces, including graphical user interfaces (GUIs), for prompt startup of a therapeutic treatment.

This disclosure describes systems and methods for displaying alarms to a clinician in a ventilatory system. Specifically, embodiments described herein seek to optimize the informative presentation of alarms on a ventilator interface. Embodiments of the present disclosure may provide one or more selection elements, each selection element indicating a ranked alarm event. The ranking of an alarm event may be determined by alarm level. If two alarm events are associated with the same alarm level, the ranking of the alarm events may be determined by parameter priority. Alarm event ranking is communicated by display in a hierarchical structure. When an alarm event ranking changes, the alarm event may shift up or down the hierarchical structure, depending on whether the ranking increased or decreased.

As such, the present disclosure provides an institution or clinician with optimal control over routine ventilatory settings. Specifically, routine layout configuration settings may be preconfigured according to a hospital-specific, clinic-specific, physician-specific, or any other appropriate protocol. Moreover, layout configuration settings may be changed and edited in response to a particular patient's changing needs and/or condition.

Figure 1:
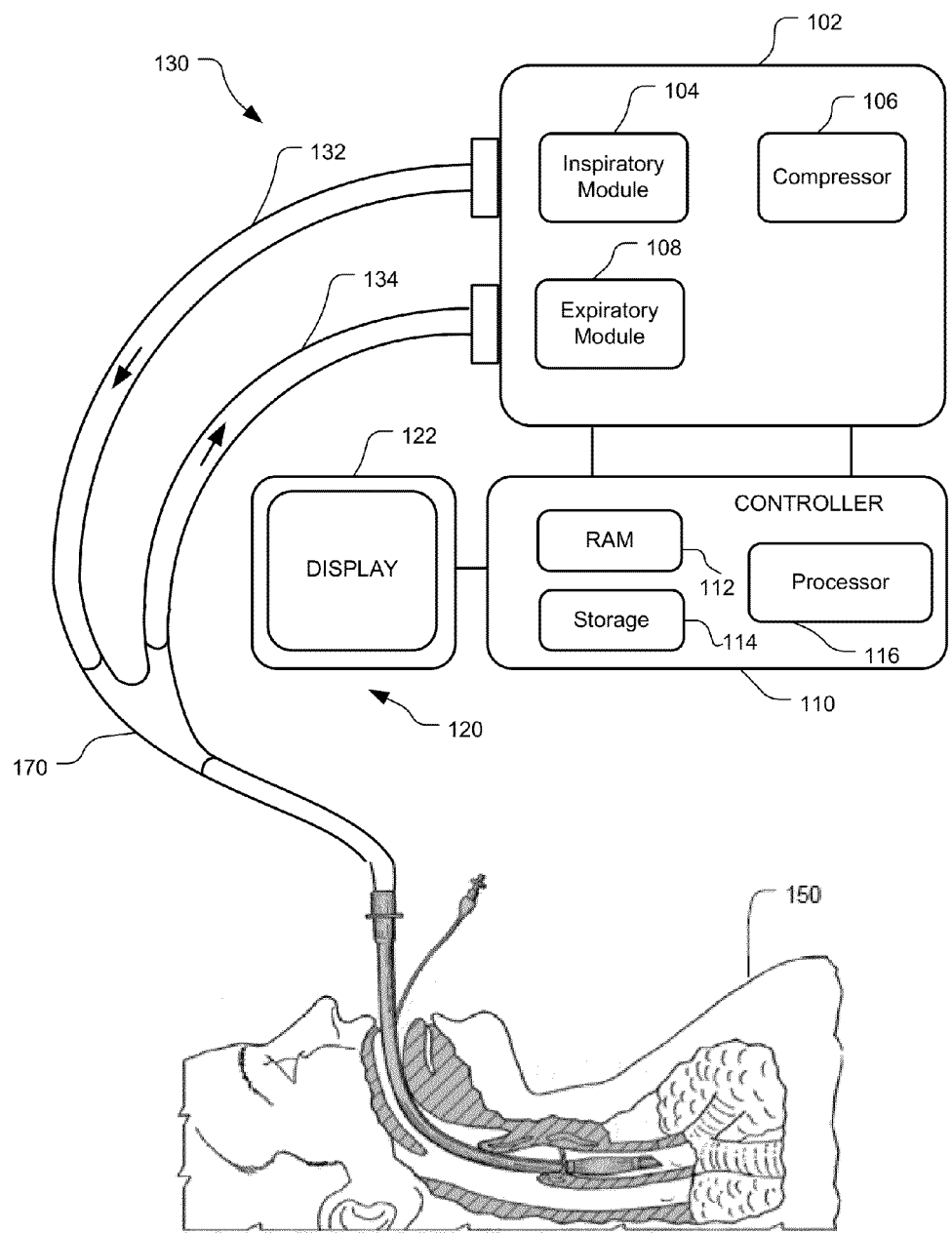
FIG. 1 is a diagram illustrating an embodiment of an exemplary ventilator connected to a human patient.

FIG. 1 illustrates an embodiment of a ventilator connected to a human patient 150. The ventilator includes a pneumatic system 102 (also referred to as a pressure generating system 102) for circulating breathing gases to and from patient 150 via the ventilation tubing system 130, which couples the patient to the pneumatic system via an invasive patient interface (e.g., endotracheal tube).

Ventilation tubing system 130 may be a two-limb (shown) or a one-limb circuit for carrying gas to and from the patient 150. In a two-limb embodiment as shown, a fitting, typically referred to as a "wye-fitting" 170, may be provided to couple the patient interface to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system may include a variety of other components, including sources for pressurized air and/or oxygen, mixing modules, valves, sensors, tubing, accumulators, filters, etc. Controller 110 is operatively coupled with pneumatic system 102, signal measurement and acquisition systems, and an operator interface 120 that may enable an operator to interact with the ventilator (e.g., reset alarms, change ventilator settings, select operational modes, view monitored parameters, etc.). Controller 110 may include memory 112, one or more processors 116, storage 114, and/or other components of the type commonly found in command and control computing devices.

The memory 112 is computer-readable storage media that stores software that is executed by the processor 116 and which controls the operation of the ventilator. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. Computer-readable storage media includes volatile and non-volatile, removable and non-removable media implemented in any method or technology for storage of information such as computer-readable instructions, data structures, program modules or other data. Computer-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As described in more detail below, controller 110 may monitor pneumatic system 102 in order to evaluate the condition of the patient and to ensure proper functioning of the ventilator based on various parameter settings. The specific parameter settings may be based on preconfigured settings applied to the controller 110, or based on input received via operator interface 120 and/or other components of the ventilator. In the depicted example, operator interface 120 includes a display 122 that is touch-sensitive, enabling the display to serve both as an input and output device.

Figure 2:
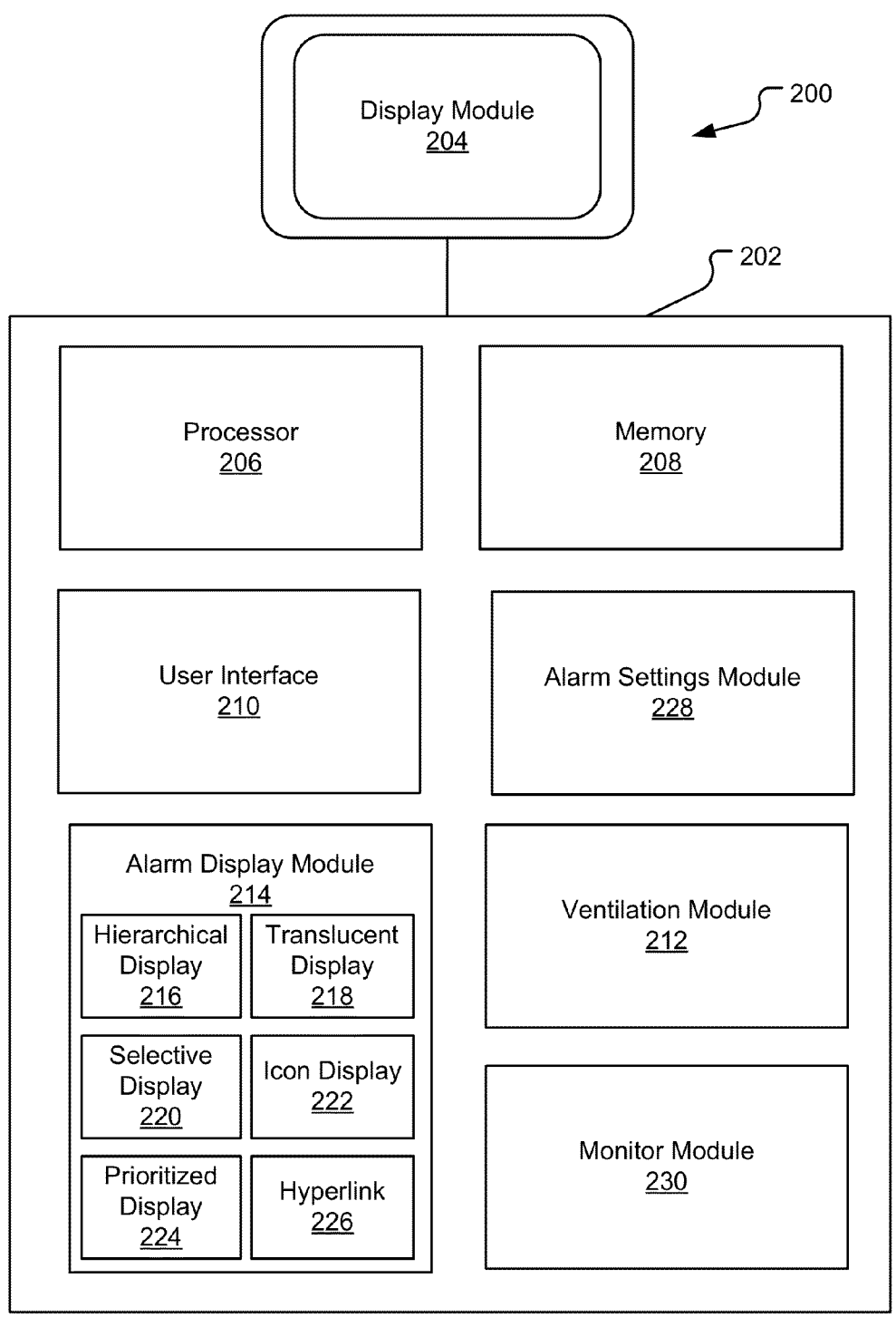
FIG. 2 is a block-diagram illustrating an embodiment of a ventilatory system having a graphical user interface for displaying structured and informative alarms.

FIG. 2 is a block-diagram illustrating an embodiment of a ventilatory system 200 having a graphical user interface for displaying structured and informative alarms.

The ventilator 202 includes a display module 204, memory 208, one or more processors 206, user interface 210, and ventilation module 212. Memory 208 is defined as described above for memory 112. Similarly, the one or more processors 206 are defined as described above for the one or more processors 116. Ventilation module 212 may oversee ventilation as delivered to a patient according to the ventilatory settings prescribed for the patient. For example, ventilation module 212 may deliver pressure and/or volume into a ventilatory circuit, and thereby into a patient's lungs, by any suitable method, either currently known or disclosed in the future.

The display module 204 presents various input screens and displays to a clinician, including but not limited to one or more structured alarm displays, as will be described further herein, for receiving clinician input and for displaying useful clinical data and alerts to the clinician. The display module 204 is further configured to communicate with user interface 210. The display module 204 may provide various windows and elements to the clinician for input and interface command operations. Additionally, user interface 210 may accept commands and input through display module 204 and may provide useful alarm information to the clinician through display module 204. Display module 204 may further be an interactive display, whereby the clinician may both receive and communicate information to the ventilator 202, as by a touch-activated display screen. Alternatively, user interface 210 may provide other suitable means of communication with the ventilator 202, for instance by a keyboard or other suitable interactive device.

Alarm display module 214 may be useful for providing comprehensive alarm information and access to alarm settings and data on a graphical user interface (GUI) of the ventilator, as may be provided by display module 204. Specifically, a hierarchical alarm structure may be provided in which a summarized alarm message may be initially presented and, upon clinician selection, an additional detailed alarm message may be displayed. The summarized alarm message may further provide comprehensive information to the clinician in abbreviated form, for example the seriousness of an alarm message may be communicated via various icons and exclamation indicators and the priority of the alarm message vis-à-vis other alarm messages may be communicated via the relative graphical placement of the alarm message.

Additionally, a summary and/or detailed alarm message may provide immediate access to the display and/or settings window associated with an alarm event. For example, an associated alarm settings window may be accessed from an alarm message via a hyperlink such that the clinician may reconfigure alarm conditions as necessary. The alarm settings window allows a clinician to view patient information for various ventilatory parameters, even those parameters that are not currently associated with an alarm event. In this way, the clinician may access additional information regarding patient respiration.

In order to accomplish the various aspects of the hierarchical informative alarm display, the alarm display module 214 may communicate with various other components and/or modules. For instance, an alarm settings module 228 may be provided. Alarm settings module 228 may monitor the various settings and other input provided by a clinician to the ventilator via the user interface 210 or display module 204. Alarm settings module 228 may compare and evaluate parameter settings entered by the clinician according to any suitable method or procedure. For example, alarm settings module 228 may detect when patient settings are missing or otherwise inappropriate for a particular input field. Inappropriate parameter settings may be indicated where settings entered for different parameters are inconsistent, e.g., one parameter setting indicates that the patient is a child, while another parameter setting indicates that the patient is an adult male, etc. In addition, alarm settings module 228 may evaluate parameter data received from monitor module 230 against the settings associated with the monitored parameters. When alarm settings module 228 determines that the parameter data falls outside applicable settings and ranges, alarm settings module 228 may communicate with alarm display module 214, or other modules of the alarm display module 214, in order to generate an informative alarm message.

Alarm display module 214 may also be configured with a hierarchical display module 216. The hierarchical display module 216 may be in communication with the monitor module 230 and/or alarm settings module 228 to receive an indication that an alarm event has occurred. The hierarchical display module 216 may be responsible for generating a multi-level alarm message via any suitable means. For example, a first level summary alarm message may be provided as a tab, banner, dialog box, or other similar type of display. Further, a summary alarm messages may be provided along a border of the graphical user interface that is either blank or that displays minimally important information. The shape and size of the summary alarm message may also be optimized for easy viewing with minimal interference. The summary alarm message may be further configured with a combination of icons and text such that the clinician may readily identify the priority of the alarm message.

Hierarchical display module 216 may be preconfigured with various summary messages or alarm descriptions corresponding to each general type of alarm event. General summary messages may also be preconfigured to provide abbreviated information to a clinician. For example, when a pressure reading indicates that the peak pressure setting has been breached, an abbreviated summary message may be displayed: "↑$P_{peak}$." This abbreviated summary message may provide both an indication that a high limit was breached, i.e. by the ↑ indicator, and an abbreviated indication of the particular breached parameter, i.e. by the $P_{Peak}$ notation. The same general summary message may also include explanatory information regarding the particular breach, for instance: "↑$P_{Peak}$–High Inspiratory Pressure." In general, a summary level alarm message may be provided in any suitable position on the screen, by any suitable means, such that a general description of an alarm event and/or its gravity may be efficiently communicated to a clinician.

The hierarchical display module 216 may also generate a selectively accessed second level alarm message. The second level alarm message may provide additional details and information regarding the alarm event and may be accessible from the first level summary alarm message. Second level alarm messages may be preconfigured with a detailed alarm message or description corresponding to various types of alarm events. For example, a detailed alarm message may provide possible reasons for an alarm breach, suggested checks or procedures for mitigating the alarm, or other helpful information. Additionally, other embodiments may provide for semi-custom detailed alarm messages. For instance, portions of a detailed alarm message may be preconfigured for similar types of alarm events, while other portions may provide variable fields that may be populated with more specific information regarding a particular breach, for instance the extent that a parameter was breached, the number of breaths over which the breach occurred, whether a maximum or minimum parameter setting was breached, etc.

Alarm display module 214 may also be configured with a translucent display module 218. Translucent display module 218 may allow for display of the summary alarm message and/or the detailed alarm message such that displayed respiratory data may be visualized behind the alarm message. This feature may be particularly useful for displaying the detailed alarm message. As described previously, alarm messages may be displayed in areas of the display screen that are either blank or that cause minimal distraction from the respiratory data and other graphical representations provided by the GUI. However, upon selective expansion of a detailed alarm message, respiratory data and graphs may be at least partially obscured. As a result, translucent display module 218 may provide the detailed alarm message such that it is partially transparent. Thus, graphical and other data may be visible behind the detailed alarm message.

Alarm display module 214 may also be configured with a selective display module 220. As discussed above, a detailed alarm message may be selectively displayed in order to offer additional information or details regarding an alarm event to a clinician. According to some embodiments, the second level detailed alarm message may be activated by clicking on the first level display message, touching a portion of the message, or otherwise. Additionally or alternatively, the first level summary alarm message may provide an arrow, or some other feature or icon for selection or activation of the detailed alarm message. Thus, a general summary alarm message may expand upon selection to provide a detailed alarm message. The detailed alarm message may be provided as a tab, banner, dialog box, or other similar type of display, which may extend from behind the general summary alarm message upon selection. In addition, according to some embodiments, the detailed alarm message may be condensed upon selection of an arrow, or some other feature or icon, via touching, clicking, or otherwise. Upon clearing or otherwise resetting an alarm following an alarm event, the summary alarm message and the detailed alarm message may also be cleared from the graphical user interface.

Alarm display module 214 may also be configured with an icon display module 222. Icon display module 222 may provide various icons and other identifiers that may communicate additional abbreviated information to a clinician, for instance regarding the alarm level. An alarm level reflects the seriousness or priority of an alarm message. For instance, "!!!" may be represented in a corner, or other visible area, of the general summary message and may indicate that the alarm is a "High" alarm level and, therefore, is relatively serious. Alternatively, while "!!" or "!" may indicate that the alarm is a "Medium" or "Low" alarm level and is, therefore, less serious. In other embodiments, a number, letter, or other priority icon may be provided to communicate the priority of an alarm message vis-à-vis other displayed alarm messages. In still other embodiments, a status icon may be provided such that the status of an alarm message may be communicated, for instance, an active status or an inactive status, a high or low status, etc. Status may also refer to the number of times during a time period that the same alarm has occurred. In still other embodiments, an up-arrow, e.g., "∇," or a down-arrow, e.g., "↓," may be provided to communicate whether a high or low limit was breached, respectively. Indeed, any number or combination of icons or other indicators may be employed to communicate additional, abbreviated information to a clinician, Alarm display module 214 may also be configured with a prioritized display module 224. As noted above, multiple alarm events may occur at the same or similar time. In this case, it may be useful for the clinician to readily determine which alarm events are of higher priority and should be addressed more quickly. The present disclosure provides for presentation of one or more pending alarms events in a vertical array, for example, that may convey an alarm event ranking and/or status. According to some embodiments, higher ranked alarm events may be presented above other alarm events. Thus, based on a graphical placement of alarm events relative to other alarm events, additional information regarding the priority or status of alarm events relative to other alarm events may be communicated to a clinician.

As will be discussed in further detail below, prioritized display module 224 is configured to rank an alarm event. The ranking of an alarm event determines whether the alarm event will be displayed in an alarm tab and, if so, where the alarm tab displaying the alarm event will be placed in the hierarchical display structure. Alarm event ranking is based on first, an alarm level and second, a parameter priority. An alarm event with a "High" alarm level will be assigned a higher ranking than an alarm event with a "Medium" or "Low" alarm level. If two alarm events have the same alarm level, ranking will be based on a predetermined parameter priority. Each ventilator parameter is assigned a priority. The assignment of parameter occurring may be done by a clinician during ventilator setup. A parameter priority may also be assigned automatically according to a hospital protocol. When two alarm events have the same alarm level, the alarm event with the higher parameter priority will be assigned the higher ranking.

Alarm display module 214 may also be configured with a hyperlink module 226. Hyperlink module 226 may be configured to provide access from the various hierarchical alarm messages to various settings and display screens associated with an identified alarm event. For example, an icon or other link indicator may be provided in either the summary alarm message and/or the detailed alarm message that may be activated or otherwise selected. Upon selection, the icon may provide direct access, via a hyperlink or otherwise, to associated settings or display screens corresponding to a particular alarm event. When access to a settings screen is provided, the clinician may reset the alarm following clinician intervention or may reconfigure alarm settings as appropriate. When access to a display screen is provided, the clinician may view additional information and respiratory data regarding the alarm event. Hyperlink module 226 may further provide access to any useful display screen, settings screen, or other graphical user interface available on the ventilator that is associated with a particular alarm event.

Monitor module 230 may operate to monitor the physical condition of the patient in conjunction with the proper operation of the ventilator 202. The monitor module 230 may communicate with display module 204, user interface 210, alarm display module 214, or other suitable modules or processors of the ventilator 202. Specifically, monitor module 230 may communicate with alarm display module 214 and/or display module 204 such that information regarding alarm events may be displayed to the clinician. Monitor module 230 may further utilize one or more sensors to detect changes in various physiological or mechanical parameters. Indeed, any sensory or derivative technique for monitoring the physical condition of the patient or the mechanical operation of the ventilator may be employed in accordance with embodiments described herein.

Figure 3:
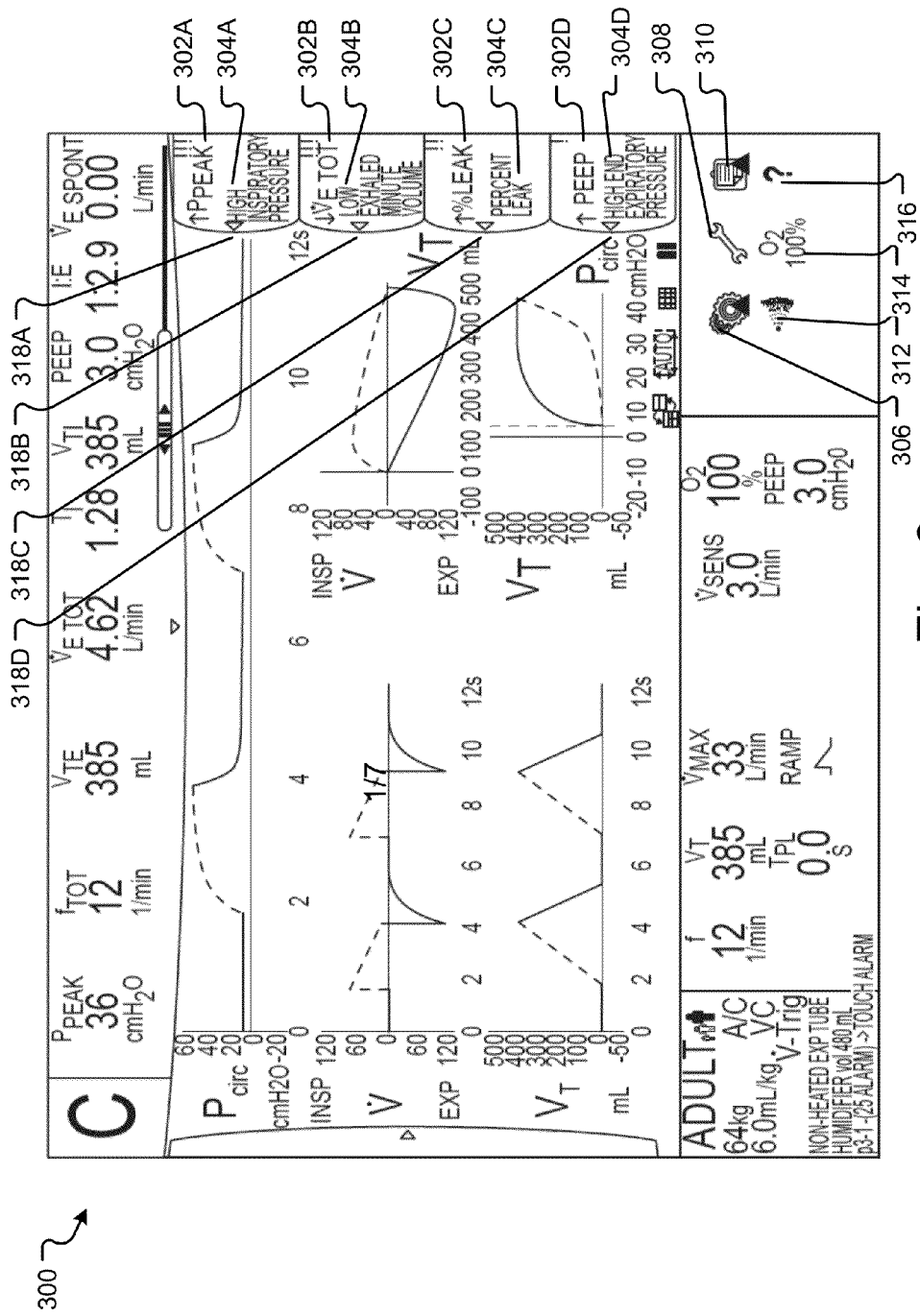
FIG. 3 is an illustration of an embodiment of a user interface for hierarchically indicating alarms on a graphical display.

FIG. 3 is an illustration of an embodiment of a user interface 300 for hierarchically indicating alarms on a graphical display.

User interface may be accessed via any suitable means, for example via a main ventilatory user interface on display module. As illustrated, user interface may provide one or more windows for display and one or more elements for selection and/or input. Windows may include one or more elements and, additionally, may provide graphical displays, instructions, or other useful information to the clinician. Elements may be displayed as buttons, tabs, icons, toggles, or any other suitable visual access element, etc., including any suitable element for input selection or control.

User interface 300 may include various icons for controlling the ventilator. These icons are selectable elements wherein selection results in display of a new window. Some exemplary control icons include a setup icon 306, a tools icon 308, a log icon 310, an alarm adjustment icon 312, an oxygen concentration icon 314, and a help icon 316. While each of these icons controls ventilatory function, only the setup icon 306 and log icon 310 will be discussed in detail below in relation to indicating alarms on a ventilator display.

According to one embodiment, as illustrated in FIG. 3, a user interface 300 is provided that includes one or more hierarchically structured alarm tabs 302A-D. The alarm tabs 302A-D are selectable elements that provide a summarized alarm message. As depicted in user interface 300, the alarm tabs 302A-D are stacked one on top of another in a hierarchical structure on the right side of user interface 300. As will be appreciated by one skilled in the art, the alarm tabs can be located on any side of user interface 300 and can be arranged in any hierarchical structure as contemplated within the scope of the present disclosure. Furthermore, user interface 300 displays four alarm tabs 302A-D. As will also be appreciated by one skilled in the art, the user interface 300 may display any number of alarm tabs.

Each of the four alarm tabs 302A-D provides an alarm message that summarizes an alarm event 304A-D. An alarm event corresponds to a change in a ventilatory parameter that causes the controller 110 monitoring the parameter to issue an alarm. For example, alarm tab 302A provides an alarm message that summarizes an alarm event 304A related to the Peak Pressure parameter as indicated by the abbreviation "$P_{Peak}$" on the alarm tab 302A. As also indicated on alarm tab 302A, the alarm event 304A that caused the alarm was an increase in Peak Pressure. This alarm event 304A is indicated on alarm tab 302A in two different manners. First, an upwards arrow next to the "$P_{Peak}$" abbreviation signifies that Peak Pressure has increased. Second, the words "High Inspiratory Pressure" are also displayed on alarm tab 302A to signify the alarm event 304A. As will be appreciated by one skilled in the art, any number of methods of indicating an alarm event on an alarm tab is contemplated as within the scope of the present disclosure.

Each of the four alarm tabs 302A-D summarizes an alarm message that corresponds to an alarm event 304A-D that is different from the alarm event corresponding to another alarm tab 302A-D. As discussed above, alarm tab 302A corresponds to a "High Inspiratory Pressure" alarm event 304A. Alarm tab 302B, on the other hand, corresponds to "Low Exhaled Minute Volume" 304B.

Each alarm tab 302A-D also displays the alarm level associated with the alarm event 304A-D in the summarized alarm message. In one embodiment, the alarm levels are indicated by one or more exclamation points on the alarm tab. For example, user interface 300 displays three different alarm levels each indicated by different numbers of exclamation points. A "High" alarm level is indicated by three exclamation points ("!!!"). A "Medium" alarm level is indicated by two exclamation points ("!!"). A "Low" alarm level is indicated by one exclamation point ("!"). Furthermore, multiple methods of indicating alarm level can be simultaneously employed by user interface 300. For example, user interface might also color tabs differently based on alarm level. In one embodiment, an alarm tab with an alarm level of "High" is colored red, while alarm tabs with alarm levels of either "Medium" or "Low" are colored yellow. As can be appreciated by one skilled in the art, any symbol, color, or other method of alarm level indication can be used alone or in combination to indicate an alarm level.

Alarm tabs 302A-D are stacked on top of one another in a hierarchical structure based on the ranking of the alarm event 304A-D displayed by the alarm tab 302A-D. The ranking is derived from alarm level and parameter priority level. For the purpose of this disclosure, the alarm tab at the top of the stack, as exemplified by alarm tab 302A, is said to display the highest ranked alarm event. The alarm tab 302B below the alarm tab 302A displaying the highest ranked alarm event is said to display the second highest ranked alarm event. The alarm tab 302C below the alarm tab 30211 displaying the second highest ranked alarm event is said to display the third highest ranked alarm event. The alarm tab 302D below the alarm tab 302C displaying the third highest ranked alarm event is said to display the fourth highest ranked alarm event.

The ranking is derived from, first, the alarm level and second, if two alarm events have the same alarm level, from parameter priority level. An alarm event indicating an alarm level of "High" will be ranked higher than an alarm event indicating an alarm level of "Medium" which will be ranked higher than an alarm event indicating an alarm level of "Low." As illustrated by user interface 300, alarm event 304A is associated with an alarm level of "High." As a result, alarm event 304A is ranked higher than alarm events 302C and 302D that indicate alarm events with alarm levels of "Medium" and "Low" respectively. As will be discussed in greater detail below, alarm levels are parameter specific. In other words, measurements that cross a certain threshold for a first parameter may trigger a "Low" alarm level while measurements that cross the same threshold for a second parameter may trigger a "Medium" or "High" alarm level.

If two alarm tabs indicate alarm events with the same alarm level, the ranking of each alarm event is then derived from parameter priority level. A ventilator monitors a multitude of ventiltatory parameters. Each parameter is assigned a priority. The parameter priority level may be assigned by a clinician or based on uniform protocol at ventilator setup. The priority level associated with a parameter is stored by the ventilator in storage 114 or RAM 112 of the controller 110. In one embodiment, the parameter priority level can be changed by utilizing setup icon 306.

As illustrated in user interface 300, when two alarm events 302A and 302B have the same alarm level ("High"), one alarm event 302A is still ranked higher than the other alarm event 302B. In the case of exemplary user interface 300, alarm event 304A is ranked higher than alarm event 304B because parameter "$P_{Peak}$" is assigned a higher priority than parameter "$V_{E\ TOT}$." As such, alarm event 304A is displayed in alarm tab 302A and alarm event 304B is displayed in alarm tab 304B.

An alarm level associated with an alarm event can increase or decrease over time. For example, a patient's condition may improve, causing the alarm level to either decrease or disappear entirely. This is known as alarm level de-elevation. Alternatively, a patient's condition may worsen, causing the alarm level to increase. This is known as alarm level elevation. When the ventilatory system detects a de-elevation or elevation of an alarm event, a clinician or other ventilatory user is notified of the change by a warning symbol superimposed on setup icon 306 and/or log icon 310. In one embodiment, the warning symbol is a yellow triangle, as exemplified in user interface 300. As will be appreciated by one skilled in the art, any symbol, word, sound, or other notification method may be used to notify the clinician that an alarm event has changed. It should be noted that a change in an alarm event may or may not be displayed on alarm tabs 302A-D depending on whether the alarm event is ranked high enough for display. The ventilator removes the warning symbol from an icon when clinician selects that icon. Selection of setup icon 306 causes user interface 300 to display alarm setup window 500. Alarm setup window 500 will be discussed in detail with regard to FIG. 5 below. Selection of log icon 310 causes user interface 300 to display alarm log window 600. Alarm log window 600 will be discussed in detail with regard to FIG. 6 below.

When an alarm level associated with an alarm event elevates to de-elevates, the change may trigger an increase or decrease in that alarm events ranking as well as the ranking of other alarm events. Changes to the ranking of alarm events necessitates that the alarm events be reordered in the user interface. As will be appreciated, reordering alarm events may cause the user interface 300 to display a previously undisplayed alarm event in an alarm tab or remove from display an alarm event previously displayed in an alarm tab.

As alarm events 304A-D are reordered in the hierarchical structure, the alarm tabs displaying the alarm events slide up and down passed one another to reflect the reordered alarm events. For example, the ventilator may detect an elevation in alarm level for alarm event 304D "High End Expiratory Pressure" from "Low" to "Medium." The elevated alarm level results in two alarm events 304C and 304D with "Medium" alarm levels. To determine the ranking of each alarm event, the system compares the parameter priority of "%LEAK" to the parameter priority for "PEEP." In one embodiment, "PEEP" has a higher parameter priority than "%LEAK." As a result, the ranking of alarm event 304D associated with "PEEP" changes from fourth highest ranked to the third highest ranked. In a similar vein, the ranking of the alarm event 304C associated with "%LEAK" changes from third highest ranked to the fourth highest ranked. Reordering of the alarm events 304C and 304D is visualized in user interface 300 by sliding the reordered alarm tabs 302D and 302C up and down, respectively, to occupy the new ranking position. Alarm tab 302D displaying alarm event 304D slides up to occupy the location of alarm tab 302C. Likewise, alarm tab 302C displaying alarm event 304C slides down to occupy the location of alarm tab 302D. In one embodiment, alarm tab 302D slides straight up while alarm tab 302C may partially retract, or partially fade, while sliding by alarm tab 302D. The alarm tabs 302A-D on user interface 300 now properly reflect the rankings of alarm events 304A-D.

As illustrated in user interface 300, alarm tabs 302A-D may be displayed by default in a minimized state. The minimized state of the alarm tab 302A-D still conveys information such as alarm event 304A-D, parameter, alarm level and ranking while not occupying too much space on the user interface. Alarm tabs may 302A-D also include an arrow 318A-D indicating that the minimized alarm tab can be expanded. Making a selection, such as by clicking, anywhere in alarm tab 312A-D will cause the selected alarm tab to expand. Expanding an alarm tab will be discussed in detail with reference to FIG. 4.

Figure 4:
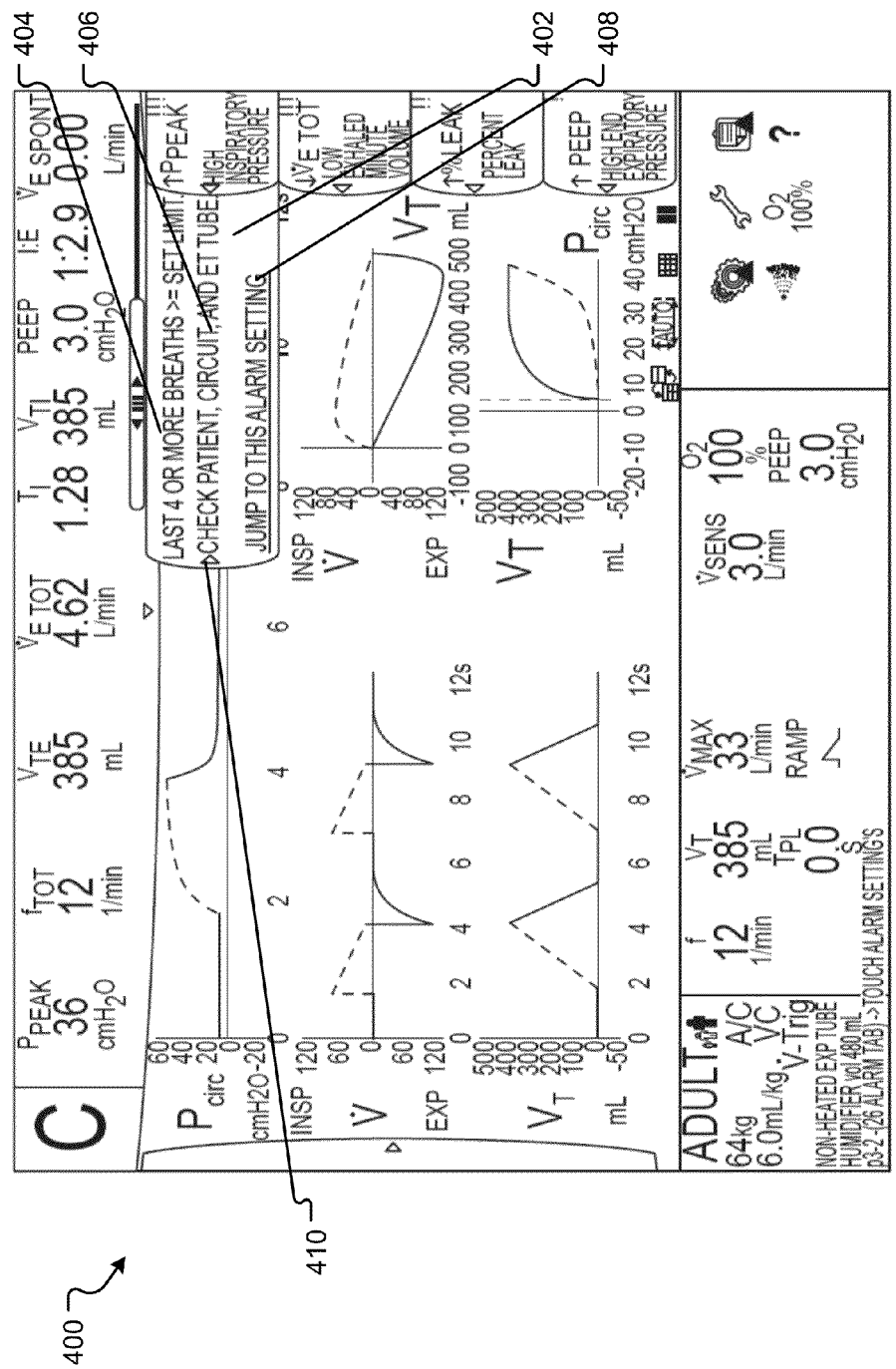
FIG. 4 is an illustration of an embodiment of a user interface for displaying an expanded alarm tab.

FIG. 4 is an illustration of an embodiment of a user interface 400 for displaying an expanded alarm tab.

With reference to like numerals from FIG. 3, FIG. 4 illustrates a user interface 400 that includes an expanded alarm tab 402. The expanded alarm tab 402 is accessed by making a selection anywhere in alarm tab 302A. Upon making the selection, the maximization arrow 318A is flipped in the opposite direction to indicate that maximization arrow is now a minimization arrow 410. When a clinician wants to deflate the expanded alarm tab 402, the clinician may make a selection anywhere in expanded alarm tab 402 and the expanded alarm tab 402 is minimized back to alarm tab 302A. Upon minimization, the minimization arrow 410 is converted back into maximization arrow 318A. User interface 400 illustrates single expanded alarm tab 402. However, as will be appreciated by one skilled in the art, any number of alarm tabs 302A-D may be expanded or minimized at any given time for display in user interface 400.

In another embodiment, certain alarm tabs associated with very high priority alarm events may be automatically expanded upon detection of the alarm event. The very high priority alarm events may be indicated by a clinician or may be industry standards. Upon initial detection of the high priority alarm event, the alarm tab will expand immediately. The clinician can then choose to minimize the expanded alarm tabs by the any of the minimization methods as discussed above. This behavior of automatically expanding alarm tabs associated with very high priority alarm events has the added advantage of maximizing the visibility of the alarm. Because the expanded alarm tab may overlap other items on screen and thus interrupt on screen activity, the behavior, in one embodiment, may only be used on alarms that require immediate intervention. This may include alarm events associated with activity outside of the ventilatory parameters such as circuit disconnect, occlusion, etc.

As is illustrated in user interface 400, expanded alarm tab 402 provides clinician with more detailed information about the alarm event. In one embodiment, expanded alarm tab 402 provides clinician with an explanation 404 as to why an alarm event is associated with a particular alarm level. For example, expanded alarm tab 402 may provide an explanation 404 for the "High" alarm level associated with alarm event 302A, stating that "Last 4 Or More Breaths>=Set Limit." This explanation 404 provides the clinician with a reason why the alarm level for the alarm event 304A is set to "High."

Expanded alarm tab 402 may also provide clinician with possible solutions 406 that may de-elevate the alarm level associated with an alarm event 304A. For example, expanded alarm tab 402 may provide possible solutions 406 to increased Peak Pressure, suggesting "Check Patient, Circuit, and ET Tube." These possible solutions 406 provide clinician with suggestions that may alleviate the problem and, as a result, de-elevate the alarm level associated with an alarm event.

Expanded alarm tab 402 may also provide the clinician with a hyperlink 408 to alarm setup window 500. The hyperlink 408 allows a clinician to "jump" to the alarm setup window 500 for that alarm without having to navigate to it through the setup icon 306.

Figure 5:
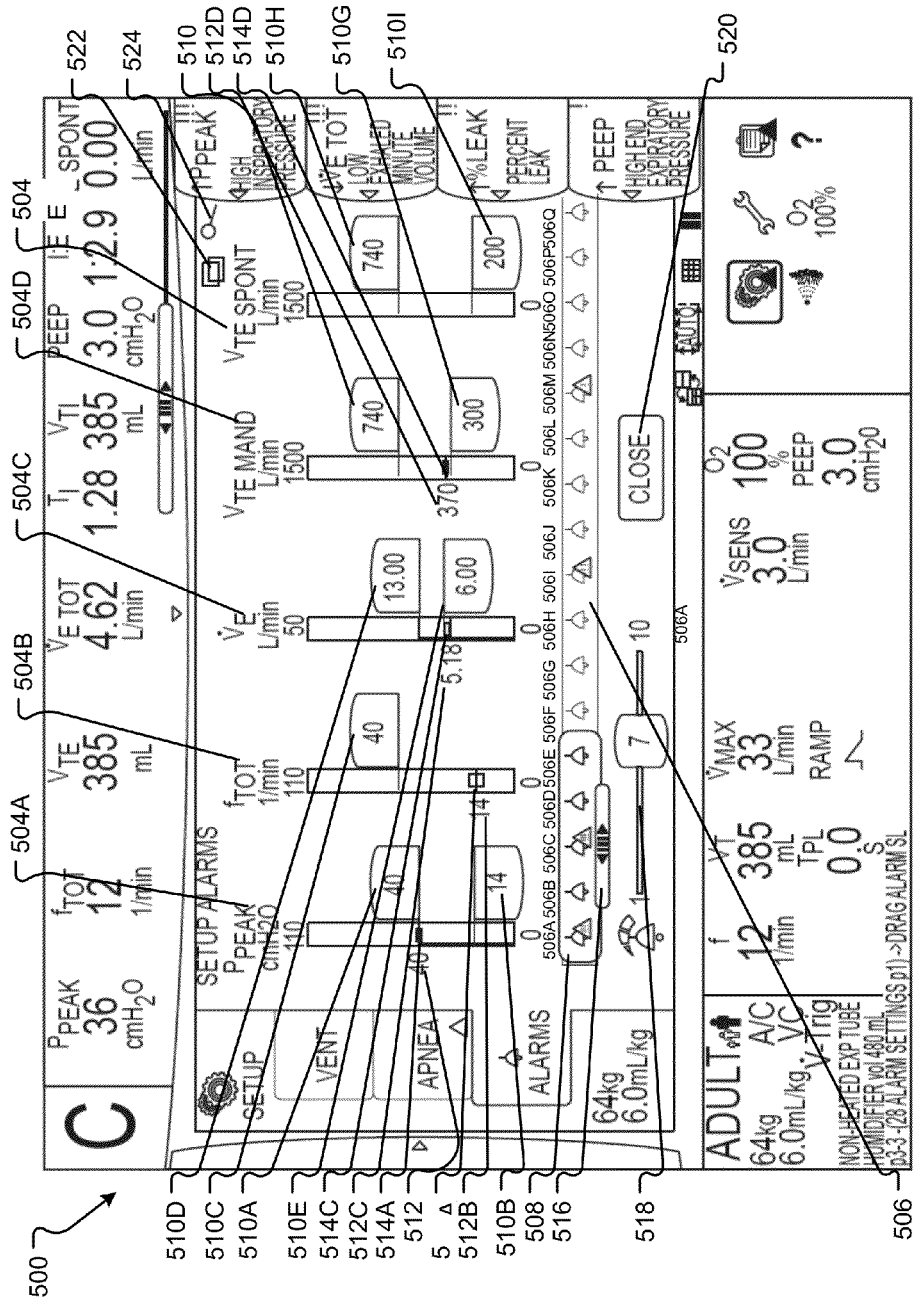
FIG. 5 depicts an alarm setup window for display in user interface.

FIG. 5 depicts an alarm setup window 500 for display in user interface 300. As discussed above, alarm setup window 500 may be accessed by selecting the hyperlink 408 in the expanded alarm tab 402. By selecting the hyperlink 408, a clinician is able to "jump" to the meter for the parameter associated with the selected alarm event. The alarm setup window 500 can also be accessed by selecting the setup icon 306 and navigating to the alarm setup window 500. As depicted by alarm setup window 500, alarm tabs 302A-D may still be visible when alarm setup window 500 is displayed.

Alarm setup window 500 displays a meter for each ventilatory parameter associated. It will be appreciated that only those alarms with user-adjustable parameters, i.e. those alarms associated with ventilatory parameters, may be associated with a meter in alarm setup window 500. Some alarms issued by the ventilator are not user-adjustable alarm such as an alarm indicating apnea, procedure error, or circuit disconnect. As discussed above, a ventilator monitors a multitude of ventilatory parameters. As such, alarm setup window 500 may display meters for parameters that are not visible on alarm tabs 302A-D in user interfere 300. Parameters may not be visible on alarm tabs 302A-D because either the parameter is not associated with an alarm event or, if the parameter is associated with an alarm event, the alarm event is not ranked high enough to be displayed in alarm tabs 302A-D. In either event, alarm setup window 500 allows a clinician to view a meter for each ventilatory parameter, whether that parameter is displayed in alarm tabs 302A-D or not.

Alarm setup window 500 displays five meters 504A-E, each meter associated with a different parameter. As discussed above, ventilator may monitor more or less than five parameters. Additional meters for parameters not currently displayed in alarm setup window 500 can be accessed using scroll bar 506. Scroll bar 506 includes multiple symbols, each symbol representing one parameter. In one embodiment, the symbols on the scroll bar 506 are bells. However, any symbol can be used within the scope of the present disclosure. Parameters associated with alarm events are further depicted on scroll bar 506 by superimposing an alarm event symbol onto the parameter symbol. As illustrated by scroll bar 506, the bells representing the parameter may be superimposed with a yellow triangle representing that the parameter is associated with an alarm event. Furthermore, the yellow triangle may include the number of exclamation points associated with the alarm level of the alarm event for that parameter. For example, a parameter with an alarm event of alarm level medium might be represented in scroll bar 506 as a bell with a yellow triangle superimposed onto in it, the yellow triangle including two exclamation points. Again, any method of representing alarm events, alarm levels, or parameters on a scroll bar 506, is contemplated within the scope of the present disclosure including differing colors, symbols, and graphical effects.

Scroll bar 506 may also include scroll bar window 508. Scroll bar window 508 encases the parameter symbols representing the parameters with meters currently displayed in alarm setup window 500. In one embodiment, alarm setup window 500 displays five meters 504A-E so scroll bar window encases five parameter symbols, 506A-E, representing the five meters. For example, the $P_{Peak}$ parameter meter 504A is displayed in the left most position of alarm setup window 500. The $P_{Peak}$ parameter meter 504A is, therefore, represented by symbol 506A in the left most position of scroll bar 506. The symbol 506A in the left most position of scroll bar 506 indicates that it represents a parameter associated with "High" level alarm event. This description matches the $P_{Peak}$ parameter which is associated with an "High" level alarm event, as indicated by alarm tab 302A.

Scroll bar window 508 can be shifted to the left or right on scroll bar 506 to display meters associated with different parameters. For example, a clinician may access scroll arrows 516 to shift scroll bar window 508 one position to the right on scroll bar 506. Such a shift would cause alarm setup window 500 to display parameters associated with symbols 506B-506F. The scroll bar window 508 can be shifted in either direction until the end of the scroll bar 506 is reached. Clinician can also access a meter for a parameter by directly selecting its symbol from scroll bar 506. For example, if clinician was interested in the "Medium" level alarm event associated with symbol 506I, the clinician could directly click on symbol 506I and alarm setup window 500 would display five meters, one being the parameter associated with symbol 506I. In one embodiment, whenever the scroll bar 506 is accessed, whether by shifting the scroll bar window 508 using scroll bar arrows 516 or by clicking a symbol on scroll bar 506, scroll bar 506 illuminates to inform a clinician of the shift.

Each meter 504A-E displays ranges and measurements associated with a particular parameter. The big numbers 510A-I indicate either an upper or lower limit of a safe range for a given parameter. The safe range is the range in which parameter measurements for a patient indicate that the patient is not in danger. For example, the $P_{Peak}$ parameter has a safe range with an upper limit 510A of 40 cmH2O and a lower limit 510B of 14 cmH2O. The $f_{TOT}$ parameter, on the other hand, has a safe range with an upper limit 510C of 40 l/min but does not have any lower limit. As a result, only one limit is displayed in association with the $f_{TOT}$ parameter meter 504B.

The upper and lower limit for each meter 504A-E can be adjusted. For example a clinician can select the upper limit MOD and drag it up or down. When upper limit MOD is released at a new value, the big numbers inside upper limit 510D will change to reflect the new value. If an upper limit 510A, C, D, F, or H is dragged to the top of the meter, the upper limit may disappear, or read "OFF". Likewise, if a lower limit 510B, E, G, or I is dragged to the bottom of the meter the lower limit may disappear, or read "OFF". An upper limit 510A, C, D, F, or H can only be dragged as low as the lower limit for that meter. Likewise, a lower limit 510B, E, G, or I can only be dragged as high as the upper limit for that meter. In another embodiment, a meter may be associated with an alarm that has a factory preset limit and cannot be turned off.

The numbers 512A-D represent the current measurement for a given parameter. For example, the current measurement for the $P_{Peak}$ parameter is 40 cmH2O. The current measurement 512A-D is displayed as a line through a white box 514A-D in the meter 504A-D for the parameter. The white box 514A-D represents the measurements of the parameter for a given period. In one embodiment, the period is a period of time, such as two minutes, and the white box represents the measurements for the parameter for the last two minutes. In another embodiment, the period is a period of breaths, such as 200 breaths, and the white box represents the measurements for the parameter for the last 200 breaths. As will be appreciated by one skilled in the art any sort of period can be used to define the bounds of the white box.

As is illustrated in alarm setup window 500, some meters may not display any measurements. In one embodiment, a meter may not display any measurement because the alarm for the parameter associated with the meter may only be required under certain breath modes or breath types. For example, in alarm setup window 500, the meter for the parameter $V_{TE\ SPONT}$ does not display any measurements. This is because the current breath mode does not require $V_{TE\ SPONT}$ measurements. In one embodiment, the alarm setup window 500 will automatically switch and begin displaying measurements for the $V_{TE\ SPONT}$ parameter when the current breath mode changes.

Alarm setup window 500 may also include one or more controls for alarm volume. As illustrated in alarm setup window 500, alarm volume may be controlled by a volume adjust scrollbar 518. By sliding volume adjust scrollbar 518 either left or right, clinician can control the volume of an emitted alarm. Volume adjust scrollbar 518 may also display the current alarm value as a numerical value. As displayed by alarm setup window 500, the alarm volume may be based on a scale from one to ten. As will be appreciated by one skilled in the art, any scale or other manner of conveying alarm value may be used as contemplated within the scope of the present disclosure.

Alarm setup window 500 also includes a transparency button 522 and a pin-up button 524. When the transparency button 522 is accessed, the alarm setup window 500 may be viewed simultaneously with other data displayed on user interface 300, or other user interface. When the pin-up button 524 is accessed, the alarm setup window 500 may remain open unless and until a clinician desires to close the alarm setup window 500 by accessing the "Close" button 520. Otherwise, the alarm setup window 500 may close automatically after some period of inactivity. In another embodiment, the alarm setup window 500 will close, and the changes to the alarm limits will be implemented, when an "Accept" button (not depicted) is accessed. When the alarm setup window 500 is pinned and the "Accept" button (not depicted) is accessed, the changes will be implemented, but the alarm setup window 500 will not be closed.

Figure 6:
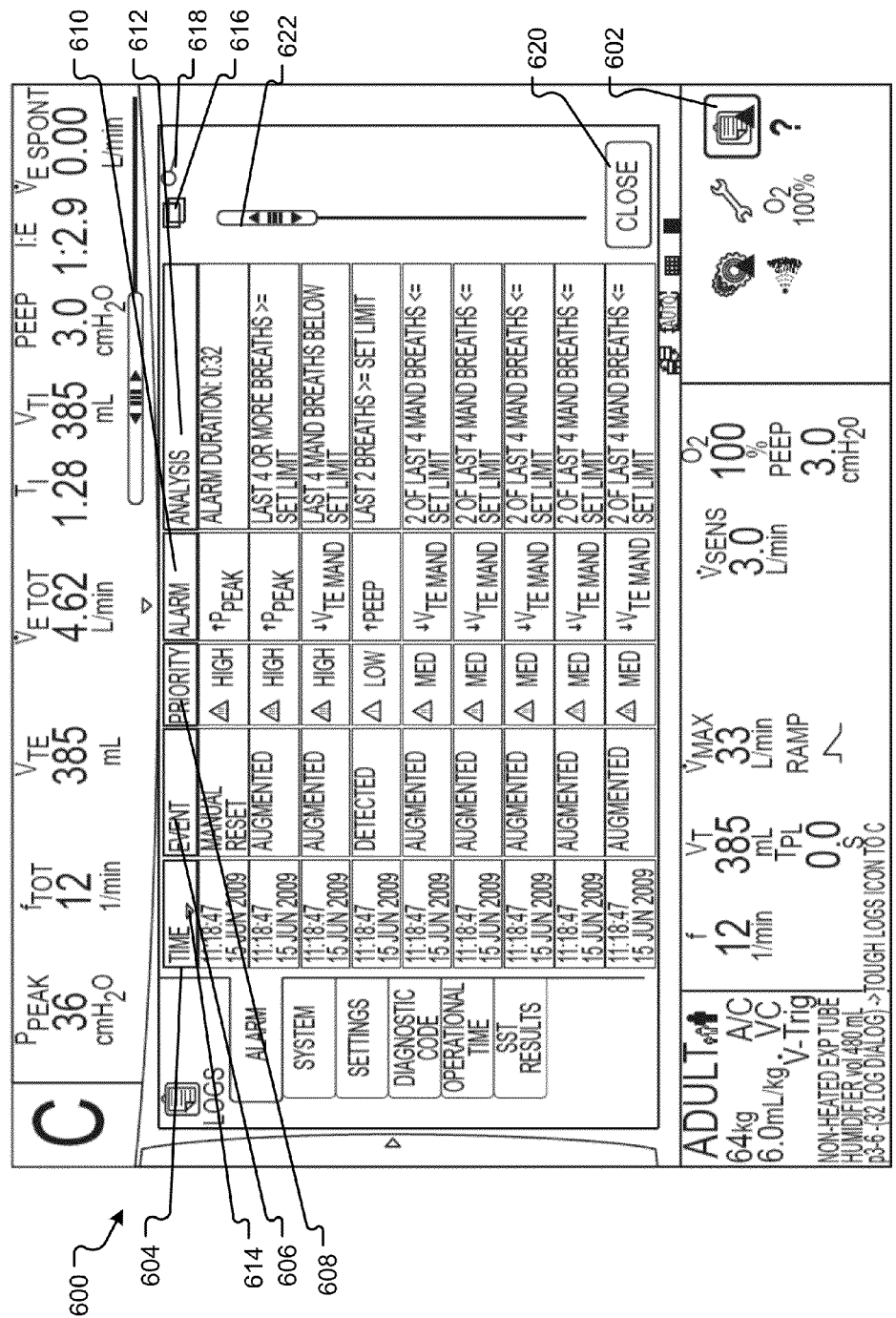
FIG. 6 depicts an alarm log window for display in user interface.

FIG. 6 depicts an alarm log window 600 for display in user interface 300. As discussed above, selection of log icon 310 causes user interface 300 to display alarm log window 600. This selection is indicated by the bold box surrounding log icon 602. As will be appreciated, any manner of indicating selection may be used.

Alarm log window 600 provides a temporal log of alarm events. In one embodiment, the alarm log records all alarm events emitted since the last manual reset of the mechanical ventilator. In another embodiment, the alarm log records all alarm events emitted since the ventilator began monitoring a new patient. A variety of information categories related to alarm events may be provided by alarm log window 600. For example, alarm log window 600 may provide information categories regarding the time 604, event 606, priority 608, alarm 610, and analysis 612. These categories may be arranged as columns in a table. In other embodiments, some or different information categories associated with alarm events may be provided by alarm log window 600.

Alarm log window 600 may provide a time 604 information category indicating the time at which an alarm event occurred. In one embodiment, the alarm events are arranged hierarchically from the most recent event to the least recent event. The time 604 information category may be accompanied by a flip arrow 614. By accessing the flip arrow 614, a clinician may flip the order the alarm log hierarchy such that the alarm events are displayed from the least recent event to the most recent event.

Alarm log window 600 may also provide an event 606 information category indicating a type of alarm event. In one embodiment, there are three types of alarm events: manual reset, augmented, and detected. However, it will be appreciated that there may be any number of alarm events. A manual reset alarm event may indicate that an alarm was manually reset by the operator pressing an alarm reset button on the ventilator. An augmented alarm event may indicate that an alarm has been escalated in priority. A detected alarm event may indicate that an alarm was first detected at that point in time.

Alarm log window 600 may also provide a priority 608 information category indicating an alarm level associated with an alarm event. As discussed above, an alarm event may be associated with an alarm level that reflects the severity of the alarm event. Exemplary alarm levels include high, medium, and low.

Alarm log window 600 may also provide an alarm 610 information category indicating a change in a parameter measurement associated with an alarm event. As discussed above, parameter names may be represented by parameter abbreviations. For example, Peak Pressure may be represented by the abbreviation "$P_{Peak}$." The parameter abbreviation may be accompanied by a symbol indicating the change in the parameter measurement. In one embodiment, the parameter abbreviation is accompanied by either an upward pointing arrow or a downward pointing arrow. For example, the "$P_{Peak}$" parameter may be accompanied by an upward pointing arrow indicating that the Peak Pressure has increased.

Alarm log window 600 may also provide an analysis 612 information category indicating more detailed information about the cause of the alarm event. The alarm 612 information category may provide the measurement that triggered the alarm event. For example, if the ventilator measures the last 4 or more breaths of the patient as greater than or equal to the set limit, the ventilator may trigger an increased Peak Pressure alarm event with a high alarm level.

Alarm log window 600 may also include a scroll bar 622. By accessing the scroll bar 622, a clinician can display different alarm events in the alarm log window 600. In one embodiment, when the scroll bar 622 is accessed it is illuminated to indicate to the clinician that the alarm events displayed in the alarm log window 600 have changed.

Alarm log window 600 may also include a transparency button 616 and a pin-up button 618. When the transparency button 616 is accessed, the alarm log window 600 may be viewed simultaneously with other data displayed on user interface 300, or other user interface. When the pin-up button 618 is accessed, the alarm log window 600 may remain open unless and until a clinician desires to close the alarm log window 600 by accessing the "Close" button 620. Otherwise, the alarm log window 600 may close automatically after some period of inactivity. When the alarm log window 600 is pinned, the changes will be implemented, but the alarm log window 600 will not be closed.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A ventilator system for hierarchically indicating one or more alarm messages corresponding to an alarm event, the ventilator system configured with a computer having a processor and a memory, the memory communicatively coupled to the processor and storing instructions that when executed by the processor cause the ventilator system to provide a graphical user interface for accepting commands and for displaying information, the graphical user interface comprising:
   at least one window associated with the graphical user interface; and
   one or more elements within the at least one window comprising one or more of:
      a first meter element for indicating a first parameter, the first parameter having a first parameter priority level;
      a second meter element for indicating a second parameter, the second parameter having a second parameter priority level;
      a scroll bar element, wherein the scroll bar is provided below the first meter element and the second meter element, the scroll bar element displaying at least:
      a first parameter symbol associated with the first parameter;
   a first alarm event symbol superimposed on the first parameter symbol, wherein the first alarm event symbol identifies a first alarm event associated with the first parameter, wherein the first alarm event has a first alarm level;
   a second parameter symbol associated with the second parameter: and
   a second alarm event symbol superimposed on the second parameter symbol, wherein the second alarm event symbol identifies a second alarm event associated with the second parameter, wherein the second alarm event has a second alarm level, and wherein the first alarm level is ranked higher than the second alarm level.

2. The ventilator system of claim 1, wherein the second parameter priority level is higher than the first parameter priority level.

3. The ventilator system of claim 2, wherein the ventilator receives an indication that the second alarm level has increased such that the second alarm level equals the first alarm level.

4. The ventilator system of claim 3, wherein the second parameter priority level is compared to the first parameter priority level.

5. The ventilator system of claim 4, wherein a determination is made that the second alarm event is now ranked higher than the first alarm event.

6. The ventilator system of claim 5, wherein the scroll bar displays an indication that the second alarm event is ranked higher than the first alarm event.

7. The ventilator system of claim 1, wherein the scroll bar further comprises a scroll bar window.

8. The ventilator system of claim 7, wherein the scroll bar window encases parameter symbols for one or more parameters for which parameter meters are displayed within the at least one window.

9. The ventilator system of claim 7, wherein the scroll bar window encases at least the first parameter symbol and the second parameter symbol.

10. The ventilator system of claim 1, wherein the scroll bar further comprises a scroll bar window, wherein the scroll bar window encases at least the first alarm symbol superimposed on the first parameter symbol and the second alarm symbol superimposed on the second parameter symbol.

11. The ventilator system of claim 1, wherein the scroll bar further displays:
 a third parameter symbol associated with a third parameter; and
 a fourth parameter symbol associated with a fourth parameter, wherein a meter element is not displayed within the at least one window for the third parameter or for the fourth parameter.

12. The ventilator system of claim 11, wherein the scroll bar further comprises a scroll bar window encasing the first parameter symbol and the second parameter symbol and not the third parameter symbol and the fourth parameter symbol.

13. A non-transitory computer-readable storage medium having instructions that when executed cause a ventilator to provide a graphical user interface for accepting commands and for displaying information, the graphical user interface comprising:
 at least one window associated with the graphical user interface; and
 one or more elements within the at least one window comprising one or more of: a first meter element for indicating a first parameter, the first parameter having a first parameter priority level; and
 a second meter element for indicating a second parameter, the second parameter having a second parameter priority level;
 a scroll bar element, wherein the scroll bar is provided below the first meter element and the second meter element, the scroll bar element displaying at least:
 a first parameter symbol associated with the first parameter;
 a first alarm event symbol superimposed on the first parameter symbol, wherein the first alarm event symbol identifies a first alarm event associated with the first parameter, wherein the first alarm event has a first alarm level;
 a second parameter symbol associated with the second parameter;
 a second alarm event symbol superimposed on the second parameter symbol, wherein the second alarm event symbol identifies a second alarm event associated with the second parameter,
 wherein the second alarm event has a second alarm level, and wherein the first alarm level is ranked higher than the second alarm level.

14. The non-transitory computer-readable storage medium of claim 13, wherein the non-transitory computer-readable storage medium is selected from: RAM, ROM, EPROM, EEPROM, flash memory, solid state memory technology, CD-ROM, DVD, optical storage, magnetic cassettes, magnetic tape, and magnetic disk storage.

15. The non-transitory computer-readable storage medium of claim 13, wherein the scroll bar further comprises a scroll bar window.

16. The non-transitory computer-readable storage medium of claim 15, wherein the scroll bar window encases parameter symbols for one or more parameters for which parameter meters are displayed within the at least one window.

17. The non-transitory computer-readable storage medium of claim 15, wherein the scroll bar window encases at least the first parameter symbol and the second parameter symbol.

* * * * *